(12) United States Patent
Jimenez et al.

(10) Patent No.: US 8,524,210 B2
(45) Date of Patent: Sep. 3, 2013

(54) PLANT-DERIVED ELASTIN BINDING PROTEIN LIGANDS AND METHODS OF USING THE SAME

(75) Inventors: Felipe Jimenez, Seal Beach, CA (US); Thomas Mitts, Visalia, CA (US); Aleksander Hinek, Toronto (CA)

(73) Assignees: Human Matrix Sciences, LLC, Visalia, CA (US); The Hospital for Sick Children, Toronto, Ontario (CA)

( * ) Notice: Subject to any disclaimer, the term of this patent is extended or adjusted under 35 U.S.C. 154(b) by 470 days.

(21) Appl. No.: 12/781,710

(22) Filed: May 17, 2010

(65) Prior Publication Data

US 2011/0237516 A1 Sep. 29, 2011

Related U.S. Application Data

(63) Continuation of application No. 11/405,843, filed on Apr. 17, 2006, now Pat. No. 7,723,308.

(60) Provisional application No. 60/737,586, filed on Nov. 17, 2005, provisional application No. 60/671,557, filed on Apr. 15, 2005.

(51) Int. Cl.
*C07K 14/00* (2006.01)
*A61K 31/00* (2006.01)

(52) U.S. Cl.
USPC ........................................ 424/78.02; 530/300

(58) Field of Classification Search
None
See application file for complete search history.

(56) References Cited

U.S. PATENT DOCUMENTS

| | | | |
|---|---|---|---|
| 4,254,105 | A | 3/1981 | Fuduka |
| 5,296,500 | A | 3/1994 | Hillebrand |
| 6,964,954 | B2 | 11/2005 | Dalko et al. |
| 2003/0054021 | A1 | 3/2003 | Dalko et al. |
| 2004/0120918 | A1 | 6/2004 | Lintner et al. |
| 2004/0162232 | A1 | 8/2004 | Mitts et al. |
| 2005/0100963 | A1 | 5/2005 | Sato et al. |
| 2005/0208150 | A1 | 9/2005 | Mitts et al. |
| 2006/0264375 | A1 | 11/2006 | Jimenez et al. |
| 2008/0050346 | A1 | 2/2008 | Jimenez et al. |
| 2009/0110709 | A1 | 4/2009 | Mitts et al. |

FOREIGN PATENT DOCUMENTS

| | | |
|---|---|---|
| EP | 2460815 A1 | 6/2012 |
| WO | WO 03/082203 A2 | 10/2003 |
| WO | WO 2004/073616 A2 | 9/2004 |

OTHER PUBLICATIONS

Grosso et al. "Peptide Sequences Selected by BA4, a Tropoelastin-Specific Monoclonal Antibody, Are Ligands for the 67-Kilodalton Bovine Elastin Receptor" 1993, *Biochemistry* 32:13369-13374.
Hinek et al. "Proteolytic digest derived from bovine *Ligamentum nuchae* stimulates deposition of new elastin-enriched matrix in cultures and transplants of human dermal fibroblasts" 2005, *J. Dermatological Science* 39(3):155-166.
Hruby et al. "Conformational and Topographical Considerations in Designing Agonist Peptidomimetics from Peptide Leads" 2000, *Curr. Med. Chem.* 9:945-970.
Hruby et al. "Synthesis of oligopeptide and peptidomimetic libraries" 1997, *Chem. Biol.* 1:114-119.
Mochizuki et al. "Signaling pathways transduced through the Elastin receptor facilitate proliferation of arterial smooth muscle cells" 2002, *J. Biol. Chem.* 277(47):44854-44863.
Morgan et al. "Approaches to the Discovery of Non-Peptide Ligands for Peptide Receptors and Peptidases" 1989, *Ann. Rep. Med. Chem.* 24:243-252.
Ripka et al. "Peptidomimetic design" 1998, *Chem. Biol.* 2:441-452.
Senior et al. "Chemotactic Responses of Fibroblasts to Tropoelastin and Elastin-derived Peptides" 1982, *J. Clin. Invest.* 70:614-618.
Senior et al. "Val-Gly-Val-Pro-Gly, a Repeating Peptide in Elastin, Is Chemotactic for Fibroblasts and Monocytes" 1984, *J. Cell Biol.* 99:870-874.
Starcher et al. "Antibody Raised to AKAAAKAAAKA Sequence on Tropoelastin Recognizes Tropoelastin but not Mature Crosslinked Elastin: A New Tool in Metabolic and Structural Studies of Elastogenesis" 1999, *Connect. Tissue Res.* 40(4):273-282.
European Search Report and Written Opinion dated Apr. 23, 2012 for EP12156977.

*Primary Examiner* — Anand Desai
(74) *Attorney, Agent, or Firm* — Pepper Hamilton LLP

(57) ABSTRACT

The present invention describes novel plant derived elastin-like peptides and peptidomimetics that may serve as functional ligands for elastin receptors and stimulate elastogenesis. The novel plant derived peptides provide an alternative (non-animal derived) source of GXXPG (SEQ ID NO. 2) containing peptides. The present invention also describes therapeutic compositions containing novel plant derived peptides or peptidomimetics useful in stimulating elastogenesis and capillary dilatation. The therapeutic compositions of the present invention that comprise novel plant derived peptides or peptidomimetics may be combined with other therapeutic agents.

14 Claims, 14 Drawing Sheets
(11 of 14 Drawing Sheet(s) Filed in Color)

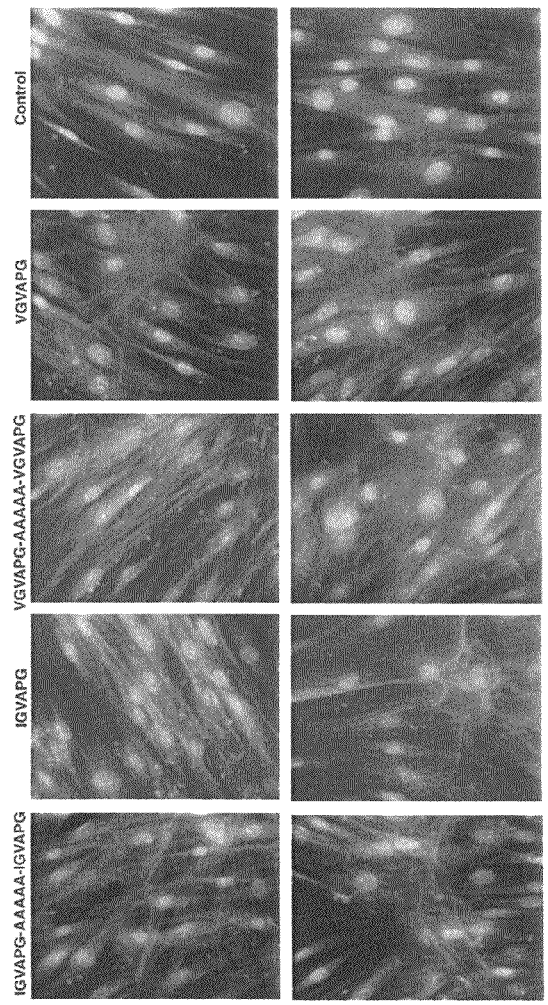
Fig. 2a
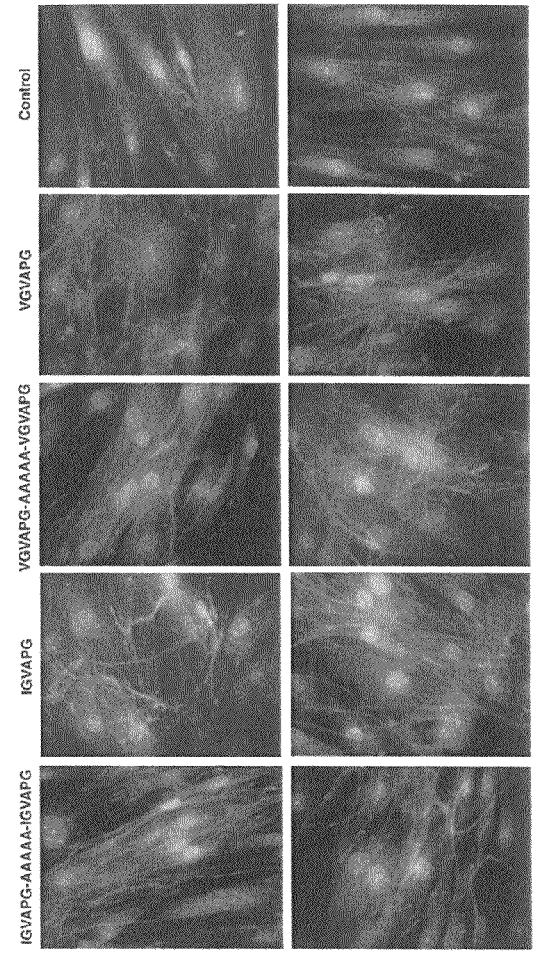
Fig. 2b
Fig. 2

FIG. 10A
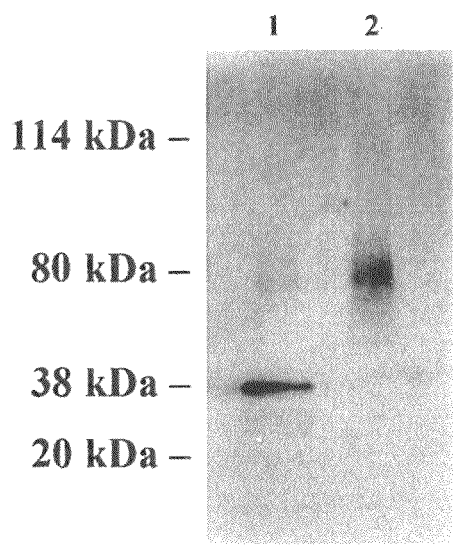
FIG. 10B
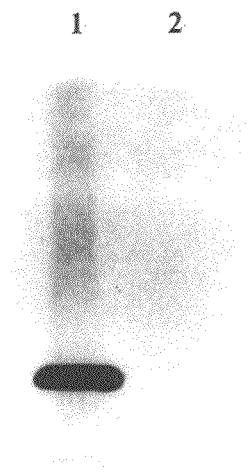
1- Amylase-digested Soluble Rice Bran
2- Amylase-digested Insoluble Rice Bran
FIG. 10

PLANT-DERIVED ELASTIN BINDING PROTEIN LIGANDS AND METHODS OF USING THE SAME

CROSS REFERENCE TO RELATED APPLICATIONS

This application is a continuation application of pending U.S. application Ser. No. 11/405,843, filed Apr. 17, 2006, which claims the benefit of U.S. Provisional Application No. 60/671,557, filed Apr. 15, 2005, and U.S. Provisional Application No. 60/737,586, filed Nov. 17, 2005, all of which are hereby incorporated by reference in their entirety.

STATEMENT REGARDING FEDERALLY SPONSORED RESEARCH OR DEVELOPMENT

Not Applicable

JOINT RESEARCH AGREEMENT

Not Applicable

INCORPORATION BY REFERENCE OF MATERIAL SUBMITTED ON A CD

Not Applicable

BACKGROUND OF THE INVENTION

Elastin is an amorphous protein present in the elastic fibers of tissues such as arteries, blood vessels, skin, tendons and elastic ligaments, the abdominal wall, and lungs. Unlike other fibrous tissues like collagen, elastin is unique in that it may be stretched to over 150 percent of its original length but it can rapidly return to its original size and shape. This property of elastin provides tissues that incorporate it the ability to resume their original form after stretching due to, for example, blood flow, breathing, or bending. Like collagen protein, elastin contains about 30% glycine amino acid residues and is rich in proline. Elastin differs from collagen in that it contains very little hydroxyproline or hydroxylysine. Elastin has a very high content of alanine and also contains two unique amino acids isodesmosine and desmosine. These amino acids are believed to be responsible for elastin's ability to return to its original shape after stretching.

A lack of elastin or genetic abnormalities affecting elastic fibers in skin, as evidenced in Costello Syndrome, Cutis Laxa and Pseudoxanthoma Elasticum, for example, lead to premature aging most noticeably characterized by wrinkling and folding of the skin in children (pre-teenage) suffering from these illnesses. Given that these conditions only affect elastic fibers in skin, it is highly probable that development of wrinkles in aged skin is due to damage to or loss of elastic fibers in skin. Unfortunately, dermal fibroblasts lose their ability to make elastin (the major component of elastic fibers) by the end of puberty. Hence, adult dermal fibroblasts cannot repair or replace damaged elastic fibers in skin later in life, leading to an essentially irreversible formation of wrinkles.

The protein motif VGVAPG (SEQ ID NO. 1) has been previously shown to stimulate proliferation/migration of monocytes, dermal fibroblasts, and smooth muscle cells through its interaction with the cell-surface elastin receptor. Other GXXPG (SEQ ID NO. 2) sequences recognized by BA4 antibody are also known ligands for the elastin receptor. More recently, it has been shown that elastin peptides, liberated through proteolytic digestion of bovine ligamentum nuchae and containing elastin receptor ligand sequences (GXXPG) (SEQ ID NO. 2) also induce elastogenesis in dermal fibroblasts through interaction with the elastin receptor.

SUMMARY OF THE INVENTION

Given the concern associated with bovine derived tissue, an alternative source of GXXPG (SEQ ID NO. 2) containing peptides that might also induce elastogenesis in dermal fibroblast cells would be useful. Embodiments of the present invention relate to a digest of plant-derived elastin-like protein and synthetic peptides mimicking these sequences detected in plants which interact with elastin receptors and appear to stimulate elastogenesis. In some embodiments, the plant-derived elastin-like protein is derived from rice bran.

The invention also comprises peptides that enhance deposition of elastin or appear to stimulate elastogenesis. In one embodiment, a peptide of the invention stimulates elastogenesis. In one embodiment, the peptide is a synthetic sextapeptide. In another embodiment, the peptide is a synthetic linked sextapeptide.

In preferred embodiments, the sextapeptide comprises the sequence $X_1$-$X_2$-$X_3$-$X_4$-$X_5$-$X_6$ (SEQ ID NO. 3), wherein $X_1$ is V or I, $X_2$ is G, $X_3$ is A or L, $X_4$ is M or S, $X_5$ is P and $X_6$ is G. In further embodiments, a linked sextapeptide is provided comprising one or more linking amino acid residues wherein the linking residues join two sextapeptide compounds, each sextapeptide having the sequence $X_1$-$X_2$-$X_3$-$X_4$-$X_5$-$X_6$ (SEQ ID NO. 3), wherein $X_1$ is V or I, $X_2$ is G, $X_3$ is A or L, $X_4$ is M or S, $X_5$ is P and $X_6$ is G. In one embodiment, the sextapeptide of the invention comprises VGAMPG (SEQ ID NO. 4), VGLSPG (SEQ ID NO. 5), IGAMPG (SEQ ID NO. 6), or IGLSPG (SEQ ID NO. 7). In one embodiment, a linked sextapeptide (or sextapeptide dimer) of the invention comprises VGAMPGAAAAAVGAMPG (SEQ ID NO. 8), VGLSPGAAAAAVGLSPG (SEQ ID NO. 9), VGVAPGAAAAAVGVAPG (SEQ ID NO. 10), IGAMPGAAAAAIGAMPG (SEQ ID NO. 11), or IGLSPGAAAAAIGLSPG (SEQ ID NO. 12).

In another embodiment, a sextapeptide is provided that comprises the sequence IGVAPG (SEQ ID NO. 13). In one embodiment, a linked sextapeptide is provided that comprises the sequence IGVAPGAAAAAIGVAPG (SEQ ID NO. 14). Another linked sextapeptide of the invention comprises the sequence of two sextapeptides having the sequence IGVAPG (SEQ ID NO. 13) that are joined by a linker.

In a further embodiment of the invention the linking moiety can be any moiety recognized by those skilled in the art as suitable for joining the sextapeptides so long as the sextapeptide compound(s) retain the ability to interact with the elastin receptor and induce elastogenesis. The linking moiety may be comprised of, for example, but not limited to, at least one of alanine or any other amino acid, a disulfide bond, a carbonyl moiety, a hydrocarbon moiety optionally substituted at one or more available carbon atoms with a lower alkyl substituent. Optimally, the linking moiety is a lysine residue or lysine amide, i.e., a lysine residue wherein the carboxyl group has been converted to an amide moiety —CONH.

The present invention also provides non-peptide or partial peptide mimetics of any of the aforementioned synthetic peptides.

Also provided are compositions comprising chemically digested plant preparations or extracts. In one embodiment, the chemically digested plant extracts comprise an elastin-like peptide that contain desmosines, crosslinking aminoacid characteristic for elastin and never reported in any plant-derived protein. In some embodiments, the chemically digested plant extracts are chemically digested rice bran extracts. In another embodiment, the chemically digested plant extracts induce or stimulate elastogenesis. In yet another embodiment, the invention comprises preparations comprising a plant-derived elastin-like protein, including an elastin-like protein from rice bran.

The invention further provides pharmaceutical compositions comprising the sextapeptides, linked sextapeptides, peptide mimetics thereof, and chemically digested plant extracts of the invention. The pharmaceutical compositions are provided in a therapeutically effective amount. The therapeutically effective amount is, in some embodiments, an amount that stimulates elastogenesis. In further embodiments, the therapeutically effective amount is an amount that stimulates proliferation and migration of dermal fibroblasts into an area of skin or tissue. The therapeutically effective amount may be, according to other embodiments, an amount sufficient to provide an appearance of increased elastogenesis in a tissue.

Also provided are methods of using the compositions of the invention. According to one embodiment, the compositions of the invention can be used to provide an appearance of increased elastogenesis in a tissue. According to another embodiment, the compositions of the invention can be used to stimulate elastogenesis.

The invention comprises methods of stimulating elastogenesis comprising administering a therapeutically effective amount of a composition of the invention. The composition of the invention can be used to improve the appearance of skin, for example, for removal of facial lines and wrinkles, as well as stretch marks of aged skin. According to one embodiment, the invention comprises a method of improving appearance of skin comprising applying a pharmaceutical composition of the invention to skin in an amount sufficient to stimulate proliferation and migration of dermal fibroblasts and elastogenesis whereby enhanced elastin deposition in said skin provides elasticity and tone to the skin. Moreover, the compositions of the invention may tighten loose, sagging skin on the face and other parts of the body including arms, legs, chest and neck areas, or give the appearance of reducing wrinkles. Other methods of use of the compounds of the present invention include stimulation of smooth muscle cells and gingival fibroblasts to produce elastin and fibrillin (oxytalan fibers), respectively, for the treatment of neointimal thickening and loosening of teeth (gingivitis), respectively.

Furthermore, the compositions may be used to enhance wound healing and to prevent and treat cutaneous hypertrophic scars. Accordingly, another embodiment of the invention includes a method of promoting wound healing and reducing scarring comprising applying a pharmaceutical composition of the invention to the wound in an amount sufficient to stimulate deposition of elastin at a site of injury wherein the elastin holds injured tissue together and reduces scarring by providing elasticity and tone to the tissue.

The compositions of the present invention may have either cosmetic or therapeutic purposes. For example, the compositions of the present invention may be used according to another embodiment to treat post infarct scar. According to this embodiment, the invention includes a method of treating post infarct scar comprising applying a pharmaceutical composition of the invention to a post infarct scar in an amount sufficient to stimulate deposition of elastin at the post infarct scar.

The file of this patent contains at least one drawing executed in color. Copies of this patent with color drawing(s) will be provided by the Patent and Trademark Office upon request and payment of necessary fee.

DESCRIPTION OF DRAWINGS

FIG. 2: Primary cultures of human dermal fibroblasts, derived from 38 and 44 year-old females, maintained for 7 days in the presence or absence of VGVAPG (SEQ ID NO. 1) (5 µg/mL), EBPL-1 (5 µg/mL), EBPL-2 (5 µg/mL) and EBPL-3 (5 µg/mL). Cells were fixed and immunostained with anti-tropoelastin antibodies and fluorescein-conjugated secondary antibodies (GAR-FITC). Two representative micrographs are shown for each condition.

FIG. 10. Both Amylase-digested soluble and insoluble rice bran preparations contain proteins that reacted with antibody raised to human tropoelastin. Additionally, the soluble bran preparation also contains a peptide with the unique AKAAA-KAAAKA (SEQ ID NO. 15) domain detected in tropoelastin.

DETAILED DESCRIPTION OF THE INVENTION

Figure 1:
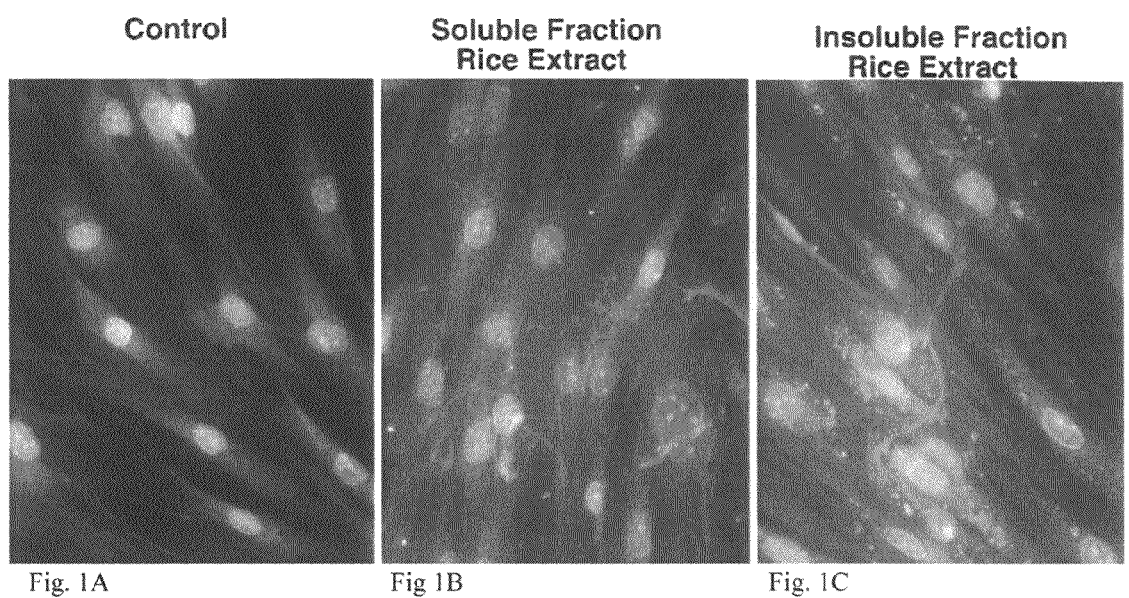
FIG. 1: Primary cultures of human dermal fibroblasts, derived from a 44 year-old female, maintained for 7 days in the presence or absence of soluble or insoluble rice bran (<3,000 daltons). Cells were fixed and immunostained with anti-tropoelastin antibodies and fluorescein-conjugated secondary antibodies (GAR-FITC). Panel A: Control. Panel B: Soluble fraction rice extract. Panel C: Insoluble fraction rice extract.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, "about 50%" means in the range of 45%-55%.

The term "cosmetic," as used herein, refers to a beautifying substance or preparation which preserves, restores, bestows, simulates, or enhances the appearance of bodily beauty or appears to enhance the beauty or youthfulness, specifically as it relates to the appearance of tissue or skin.

The term "improves" is used to convey that the present invention changes either the appearance, form, characteristics and/or the physical attributes of the tissue to which it is being provided, applied or administered. The change in form may be demonstrated by any of the following alone or in combination: enhanced appearance of the skin; increased softness of the skin; increased turgor of the skin; increased texture of the skin; increased elasticity of the skin; decreased wrinkle formation and increased endogenous elastin production in the skin, increased firmness and resiliency of the skin.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

The term "dimer", as in a peptide "dimer", refers to a compound in which two peptide chains are linked; generally, although not necessarily, the two peptide chains will be identical and are linked through a linking moiety covalently bound to the terminus of each chain.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal without the production of undesirable physiological effects such as nausea, dizziness, rash, or gastric upset. In a preferred embodiment, the therapeutic composition is not immunogenic when administered to a human patient for therapeutic purposes.

"Providing" when used in conjunction with a therapeutic means to administer a therapeutic directly into or onto a target tissue or to administer a therapeutic to a patient whereby the therapeutic positively impacts the tissue to which it is targeted. Thus, as used herein, the term "providing", when used in conjunction with compositions comprising one or more manganese salts, can include, but is not limited to, providing compositions comprising one or more divalent manganese based compounds, trivalent iron based compounds or salts thereof into or onto the target tissue; providing compositions systemically to a patient by, e.g., intravenous injection whereby the therapeutic reaches the target tissue; providing compositions in the form of the encoding sequence thereof to the target tissue (e.g., by so-called gene-therapy techniques).

Unless otherwise indicated, the term "skin" means that outer integument or covering of the body, consisting of the dermis and the epidermis and resting upon subcutaneous tissue.

As used herein, the term "therapeutic" means an agent utilized to treat, combat, ameliorate, prevent or improve an unwanted condition or disease of a patient. In part, embodiments of the present invention are directed to improve the functionality, the appearance, the elasticity, and/or the elastin content of mammalian tissue. As it applies to skin, it is measured by elasticity, turgor, tone, appearance, degree of wrinkles, and youthfulness. As it applies to smooth muscle cells, blood vessels, it is measured by increased elasticity (elastin/elastic fiber synthesis and deposition) and decreased neointimal thickening (smooth muscle cell proliferation). The methods herein for use contemplate prophylactic use as well as curative use in therapy of an existing condition.

The terms "therapeutically effective" or "effective", as used herein, may be used interchangeably and refer to an amount of a therapeutic composition embodiments of the present invention—e.g., one comprising one or more plant-derived peptides. For example, a therapeutically effective amount of a composition comprising plant derived peptides is a predetermined amount calculated to achieve the desired effect, i.e., to effectively promote elastin production, collagen production, cell proliferation, or improved appearance, or improved tissue elasticity in an individual to whom the composition is administered. The tissue in need of such therapeutic treatment may present lines or wrinkles, sun damaged tissue, or scar tissue.

The term "tissue" refers to any aggregation of similarly specialized cells which are united in the performance of a particular function. As used herein, "tissue", unless otherwise indicated, refers to tissue which includes elastin as part of its necessary structure and/or function. For example, connective tissue which is made up of, among other things, collagen fibrils and elastin fibrils satisfies the definition of "tissue" as used herein. Additionally, elastin appears to be involved in the proper function of blood vessels, veins, and arteries in their inherent visco-elasticity. Thus, "tissue" thus includes, but is not limited to skin fibroblasts and smooth muscle cells including human aortic smooth muscle cells.

The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., excipient, carrier, or vehicle.

For simplicity and illustrative purposes, the principles of the invention are described by referring mainly to an embodiment thereof. In addition, in the following descriptions, numerous specific details are set forth in order to provide a thorough understanding of the invention. It will be apparent however, to one of ordinary skill in the art, that the invention may be practiced without limitation to these specific details. In other instances, well known methods and structures have not been described in detail so as not to unnecessarily obscure the invention.

According to one embodiment, a composition of the invention comprises a sextapeptide as described herein. According to another embodiment, a composition of the invention comprises a linked sextapeptide as described herein. A composition of the invention may, alternatively, comprise a peptide mimetic of the sextapeptides or linked sextapeptides of the invention. The invention comprises, in other embodiments, chemically digested plant extracts, as described herein.

Compositions of the present invention may stimulate the synthesis of one or more of the extracellular matrix components by fibroblasts and other matrix supporting cells. For example, compositions of the invention may stimulate the synthesis of extracellular matrix components such as, but not limited to, fibrillin I, a major scaffold component of elastin, collagen type I, II, and III, fibronectin chondroitin sulfate-containing glycosaminoglycans, elastin, and lysyl oxidase. Additionally, compositions of the present invention may stimulate cell proliferation and elastin production in smooth muscle cells.

As further described herein, the compositions of the invention may provide the appearance of increased elastogenesis in a tissue. One embodiment of the present invention includes therapeutic compositions and cosmetic preparations useful in improving or enhancing the appearance of skin comprising the aforementioned synthetic sextapeptides, or peptide mimetics thereof, or chemically digested plant extracts. The compositions of the present invention may further improve facial lines and wrinkles, for example, through induction of new connective tissue synthesis in skin. The compositions are used, according to another embodiment, for the restoration of cutaneous connective tissue proteins in the skin.

In an embodiment of the present invention, compositions may be formulated into a cosmetic skin care product or cosmetic preparation to aid or facilitate the assembly of new elastic fibers in skin. Other suitable formulations include fibroblast injections for the improvement of facial lines and wrinkles. Patient dermal fibroblasts are cultured in vitro and re-introduced via injection into sites presenting visible lines and wrinkles.

The invention includes methods of using the compositions of the invention. In one embodiment, a method of stimulating the proliferation and migration of dermal fibroblasts and elastogenesis comprising administering a composition of the invention in an amount sufficient to provide the appearance of increased elastogenesis is provided. In another embodiment, a method of administering a composition of the invention in an amount sufficient to stimulate elastogenesis is provided.

Further embodiments include methods of treating premature aging, including wrinkling and folding of the skin by administering therapeutically effective amounts of a composition of the invention. Embodiments further include methods of treating elastin or genetic abnormalities affecting elastic fibers in skin, including, but not limited to, Costello Syndrome, Cutis Laxa and Pseudoxanthoma Elasticum, by administering therapeutically effective amounts of a composition of the present invention.

As described herein, we have shown that the compositions of the invention stimulate elastogenesis in cultures of stromal cells isolated from human heart. Therefore, the invention further includes uses of the compositions in the treatment of cardiovascular disorders that may benefit from stimulated elastogenesis. For example, the invention comprises methods of using the compositions of the invention to stimulate elastic fiber formation in the scars formed after heart infarcts. In the majority of patients with post-infarct scars, the scars formed contain mostly collagen fibers that are stiff and non resilient. Stimulation of local stromal cells in post-infarct heart to produce elastic fibers decreases the possibility of collagenous fibrosis and creates a stronger and more durable scar, more likely to comply with contractile heart muscle. The compositions of the invention, when injected in to hypoxic heart tissue, will not effect levels of local oxygen. The present invention, therefore, provides an advantage over other experimental protocols in which injections of millions of allogenic cells (e.g., CHO cells transfected with an elastin gene) compete for oxygen with surviving heart cells and may deteriorate net healing of post-infarct heart.

Elastin

Elastin is secreted by fibrocytes of the connective tissues into the intercellular network. In the dermal connective tissue, the elastin fibers are thin and sinuous. Elastin contained in the dermis represents 5% of its dry weight. Elastin is a large fibrous protein which is formed by spiral filaments that can be compared to springs. The spiral filaments consist of peptidic chains that can stretch out. The peptidic chains are connected to each other by very specific amino-acids: desmosin and isodesmosin, which builds between them, giving the molecule a reticular aspect. After stretching out, the molecules resume their original shape due to this cross linking, which is essential to molecular elasticity.

The biosynthesis of elastin begins with the embryonic period and continues through adulthood, at which time the body stops producing elastin. Thus, elastin is no longer renewed. With aging, the elastic fibers progressively degenerate and separate into fragments. The skin progressively loses its elasticity, resulting in fine lines and wrinkles. This damage to our elastic tissue cannot be avoided and is part of the natural (physiological) aging process. This process begins relatively early, but accelerates considerably after age 40.

Wound healing is a complex biological process that involves many different cell types, many different cytokines, the extracellular matrix (ECM), and numerous interactions among them. Most wounds heal rapidly and efficiently within a week or two; however, the result is neither aesthetically nor functionally perfect. Wound contraction and scar formation are currently unavoidable results of wound healing. Scar tissue is less flexible than normal skin and can be cosmetically disfiguring, and wound contraction can lead to joint disablement. Scars lack elastin and consist of a poorly reconstituted collagen matrix in dense parallel bundles rather than the mechanically efficient basket-weave meshwork of collagen in the unwounded dermis.

As wounds heal a new stratified epidermis is reestablished from the margins of the wound inward. Matrix formation and remodeling begins simultaneously with re-epithelialization. The matrix is constantly altered over the next several months with the elimination of the fibronectin from the matrix and the accumulation of collagen that provides the residual scar with increasing tensile strength. Elastin fibers, which are responsible for the elasticity of tissue, are only detected in human scars years after the injury.

Many methods have been proposed and tested to promote wound healing and limit scarring; however, better methods and compositions are still needed. Wounds that can be treated with the compositions of the invention include, but are not limited to, cutaneous wounds, corneal wounds, and injuries to the epithelial-lined hollow organs of the body and post-infarct heart. Wounds suitable for treatment include those resulting from trauma such as burns, abrasions and cuts, decubitus and non-healing varicose and diabetic ulcers, as well as wounds resulting from surgical procedures such as incisions and skin grafting. According to one embodiment, the compositions of the invention, for example, chemically digested plant extracts, can be used to treat infected wounds and ulcers, in which proteolytic enzymes released from dying cells and bacteria can facilitate further cleavage of peptides within a preparation and release smaller elastogenic peptides containing EBPL-like domains.

Stimulation of the deposition of elastin at the site of injury by composition of the invention will aid in promoting wound healing while limiting scarring. Initially, the stimulated deposition of elastin will hold the injured tissue together. The stimulation of elastin synthesis by a composition of the invention according to some embodiments will further act as a chemotactic attractant for fibroblasts, endothelial cells, and inflammatory cells, which will promote healing of the injured tissue. Elastin synthesis at the site of injury will also lessen scarring since scar tissue is devoid of elastin, and elastin is an important component of uninjured skin. The stimulation and secretion of elastin into the matrix will also generally provide a favorable environment for the cells that participate in the healing process, further accentuating the wound healing process.

A composition of the invention, according to one embodiment, will stimulate the migration of fibroblasts into the treated area. According to another embodiment, a composition of the invention will interact with elastin receptors on the fibroblasts and stimulate the secretion of elastin (i.e., elastogenesis). In one embodiment, a composition of the invention is applied to the wound and maintained in contact with the wound for an extended period of time, i.e., during the entire healing process or until at least closure of the wound occurs by new tissue.

Elastin owes its properties to its thin structure which resembles that of rubber. Elastin is the protein responsible for our skin's essential elasticity and tonicity. Its decrease means the skin starts sagging, allowing fine lines, folds and wrinkles to appear and grow. The present invention provides compositions comprising a sextapeptide compound, a linked sextapeptide, a peptide mimetic of either of these, or chemically digested rice bran, as a stimulator of elastogenesis. This occurs, according to some embodiments, by the composition of the invention interacting with elastin receptors and stimulating the proliferation and migration of dermal fibroblasts and other supporting cells to an area of skin in need of elastogenic properties. Such areas of skin include, but are not limited to, wounds, sagging and/or wrinkled skin, stretched skin, skin damaged by UV or other radiation or by environmental damage, etc. The compositions of the invention induce elastogenesis in dermal fibroblasts, and by their interaction with the elastin receptors, cause cells to increase the secretion of insoluble elastin fibers into the extracellular matrix. Thus, the present invention provides compositions and methods to compensate for the loss of elastic components in the dermis.

The result of aging on skin, whether or not it has been accelerated by environmental damage (such as radiation, pollution, etc.), is a deterioration of the dermal layer: fewer fibroblasts, less collagen, less elastin and less circulatory support. Consequently, normal stretching and contraction of the skin leads to damage of the dermis that is not readily corrected, resulting in wrinkling and/or sagging. The present invention provides methods and compositions for stimulating the proliferation and migration of dermal fibroblasts into an area in need of elastogenic properties. According to some embodiments, the compositions of the invention interact with elastin receptors on fibroblasts and stimulate the secretion of elastin. The enhanced elastin deposition reduces the effects of radiation (for example, but not limited to, ultraviolet radiation) or other environmental damage by providing elasticity and tone to the skin.

Elastogenic Peptides, or Peptide Mimetics Thereof

In accordance with one embodiment of the present invention, novel peptides derived from or based on protein sequences found in plants are provided. The compositions of the invention according to one embodiment provide the appearance of increased elastogenesis. In other embodiments, the compositions stimulate elastogenesis and migration of dermal fibroblasts. In one embodiment, such stimulation is the result of the interaction of the composition of the invention with elastin receptors. In one embodiment, a synthetic sextapeptide is provided, which binds to elastin receptors and stimulates elastogenesis. The peptides of the invention are also referred to herein as elastin binding protein ligands, or EBPLs.

In an embodiment of the invention, the sextapeptide comprises the sequence $X_1$-$X_2$-$X_3$-$X_4$-$X_5$-$X_6$ (SEQ ID NO. 3), wherein $X_1$ is V or I, $X_2$ is G, $X_3$ is A or L, $X_4$ is M or S, $X_5$ is P and $X_6$ is G. In one embodiment, the sextapeptide of the invention comprises VGAMPG (SEQ ID NO. 4), VGLSPG (SEQ ID NO. 5), IGAMPG (SEQ ID NO. 6), or IGLSPG (SEQ ID NO. 7).

In further embodiments, a linked sextapeptide (or sextapeptide dimer) is provided wherein two sextapeptides of the invention are joined with one or more additional linking amino acid residues (a "linking moiety"). According to one embodiment, the synthetic linked sextapeptide has the sequence $X_1$-$X_2$-$X_3$-$X_4$-$X_5$-$X_6$,-$X_7$-$X_1$-$X_2$-$X_3$-$X_4$-$X_5$-$X_6$ (SEQ ID NO. 16), wherein $X_7$ is a linking moiety; $X_1$ is independently selected from V and I; $X_2$ is G; $X_3$ is independently selected from A and L; $X_4$ is independently selected from M and S; $X_5$ is P; and $X_6$ is G. The linking moiety of a linked sextapeptide can be any moiety recognized by those skilled in the art as suitable for joining the sextapeptides so long as the sextapeptide compound(s) retain the ability to interact with the elastin receptor and induce elastogenesis. The linking moiety may be comprised of for example, but not limited to, at least one of alanine or any other amino acid, a disulfide bond, a carbonyl moiety, a hydrocarbon moiety optionally substituted at one or more available carbon atoms with a lower alkyl substituent. Optimally, the linking moiety is a lysine residue or lysine amide, i.e., a lysine residue wherein the carboxyl group has been converted to an amide moiety —CONH.

The compositions of the invention may also comprise linked sextapeptides wherein the two sextapeptides that are joined by a linker are different sextapeptides.

In one embodiment, the linked sextapeptide of the invention comprises VGAMPGAAAAAVGAMPG (SEQ ID NO. 8), VGLSPGAAAAAVGLSPG (SEQ ID NO. 9), VGVAPGAAAAAVGVAPG (SEQ ID NO. 10), IGAMPGAAAAAIGAMPG (SEQ ID NO. 11), or IGLSPGAAAAAIGLSPG (SEQ ID NO. 12). Also provided by the invention is a linked sextapeptide comprising the sequence IGVAPGAAAAAIGVAPG (SEQ ID NO. 14). Another linked sextapeptide of the invention comprises the sequence of two sextapeptides having the sequence IGVAPG (SEQ ID NO. 13) that are joined by a linker, as described above.

The present invention also provides non-peptide or partial peptide mimetics of any of the aforementioned synthetic peptides. According to another aspect of the invention, a compound that binds to elastin receptors, stimulates migration of dermal fibroblasts and additionally stimulates fibroblast elastogenesis is provided. The compound has a formula $X_1$-$X_2$$X_3$-$X_4$-$X_5$-$X_6$ (SEQ ID NO. 17), wherein $X_1$ is V or I or a mimetic of V or I; $X_2$ is G, or a mimetic of G; $X_3$ is A or L, or a mimetic of A or L; $X_4$ is M or S, or a mimetic of M or S, $X_5$ is P or a mimetic of P and $X_6$ is G or a mimetic of G. In alternative embodiments, the compound may comprise the formula $X_1$-$X_2$-$X_3$-$X_4$-$X_5$-$X_6$-$X_7$ (SEQ ID NO. 18), wherein $X_7$ is one or more linking amino acid residues comprising alanine wherein the linking residues join two sextapeptide compounds to each other, each sextapeptide having the sequence $X_1$-$X_2$-$X_3$-$X_4$-$X_5$-$X_6$ (SEQ ID NO. 17), wherein $X_1$ is V or I or a mimetic of V or I; $X_2$ is G, or a mimetic of G; $X_3$ is A or L, or a mimetic of A or L; $X_4$ is M or S, or a mimetic of M or S, $X_5$ is P or a mimetic of P and $X_6$ is G or a mimetic of G.

A further embodiment of the present invention relates to peptide mimetics of GXXPG peptides. In one embodiment, the peptides of the invention are modified to produce peptide mimetics by replacement of one or more naturally occurring side chains of the 20 genetically encoded amino acids (or D amino acids) with other side chains, for instance with groups such as alkyl, lower alkyl, cyclic 4-, 5-, 6-, to 7 membered alkyl, amide, amide lower alkyl, amide di (lower alkyl), lower alkoxy, hydroxy, carboxy and the lower ester derivatives thereof, and with 4-, 5-, 6-, to 7 membered heterocyclics. For example, proline analogs can be made in which the ring size of the proline residue is changed from 5 members to 4, 6, or 7 members. Cyclic groups can be saturated or unsaturated, and if unsaturated, can be aromatic or nonaromatic. Heterocyclic groups can contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics may also have amino acid residues that have been chemically modified by phosphorylation, sulfonation, biotinylation, or the addition or removal of other moieties.

A variety of techniques are available for constructing peptide mimetics with the same or similar desired biological activity as the corresponding native but with more favorable activity than the peptide with respect to solubility, stability, and/or susceptibility to hydrolysis or proteolysis. See, e.g., Morgan & Gainor, *Ann. Rep. Med. Chem.* 24:243-252 (1989). Certain peptidomimetic compounds are based upon the amino acid sequence of the peptides of the invention. Often, peptidomimetic compounds are synthetic compounds having a three-dimensional structure (i.e. a "peptide motif") based upon the three-dimensional structure of a selected peptide. The peptide motif provides the peptidomimetic compound with the desired biological activity, i.e., binding to PIF receptors, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life.

Peptidomimetic design strategies are readily available in the art. See, e.g., Ripka & Rich, *Curr. Op. Chem. Biol.* 2:441-452 (1998); Hruby et al., *Curr. Op. Chem. Biol.* 1:114-119 (1997); Hruby & Balse, *Curr. Med. Chem.* 9:945-970 (2000). One class of peptidomimetics a backbone that is partially or completely non-peptide, but mimics the peptide backbone atom—for atom and comprises side groups that likewise mimic the functionality of the side groups of the native amino acid residues. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics comprises a small non-peptide molecule that binds to another peptide or protein, but which is not necessarily a structural mimetic of the native peptide. Yet another class of peptidomimetics has arisen from combinatorial chemistry and the generation of massive chemical libraries. These generally comprise novel templates which, though structurally unrelated to the native peptide, possess necessary functional groups positioned on a nonpeptide scaffold to serve as "topographical" mimetics of the original peptide (Ripka & Rich, 1998, supra).

Chemically Digested Rice Bran Extracts

According to one embodiment, chemically digested plant extracts are provided that stimulate or appear to stimulate elastogenesis in a tissue. In one embodiment, such plant extracts are obtained from rice bran. The chemically digested rice bran extracts described herein were found to be immunoreactive with a panel of antibodies raised to human tropoelastin. Furthermore, chemical digests of both soluble and insoluble rice bran contained the unique crosslinking aminoacid, desmosine (1742/mg protein and 1638/mg protein respectively). These characteristics suggest the presence of one or more elastin-like peptides in rice bran. Thus, the present invention comprises such elastin-like peptide preparations, including pharmaceutical compositions and cosmetic preparations, and chemically digested rice bran preparations, as well as methods of using compositions comprising such preparations to treat the conditions discussed herein.

Pharmaceutical Compositions

In embodiments of the present invention, the compositions of the invention may be formulated into pharmaceutical compositions. For example, in one embodiment, topical carriers may be employed which should be both non-irritating to the skin and which are suitable for delivering the active components to the skin. Further, suitable topical carriers should be those which do not inhibit the antioxidant activity of the active ingredients thus reducing the efficiency of the composition for protecting the skin from the effects of free radical damage which can occur due to, for example, acute and chronic ultraviolet radiation. Further, such carriers must be of sufficiently high purity and sufficiently low toxicity to render them suitable for chronic topical administration to the skin and be free of bacterial contaminants.

The compositions of the invention described herein can be incorporated into any suitable pharmacologically acceptable carrier which is suitable for topical administration to the human skin. As such, the pharmacologically acceptable carrier must be of sufficient purity and have sufficiently low toxicity to render it suitable for administration to a human noting that, generally, the carrier can represent up to 99.99% and typically from at least approximately 80% of the total composition. Thus, the phrase "pharmaceutically acceptable" refers to molecular entities and compositions that do not produce an allergic or similar untoward reaction when administered to a human. The pharmaceutically acceptable carriers and additives employed in the present compositions are compatible with the compositions of the invention.

Typical compositions for use herein include a wide variety of physical forms. These include, but are not limited to, solutions, lotions, creams, oils, gels, sticks, sprays, ointments, balms, patches and pastes. Generally, such carrier systems can be described as being solutions, creams, emulsions, gels, solids and aerosols.

Solvents are generally employed in the preparation of suitable topical compositions. Such solvents can either be aqueous or organic based and, in either case, the solvent must be capable of having dispersed or dissolved therein the above-described active components while not being irritating to the user. Water is a typical aqueous solvent while suitable organic solvents include propylene glycol, battalion glycol, polyethylene glycol, polypropylene glycol, glycerol, 1,2,4-butanetriol, sorbitol esters, 1,2,6-hexanetriol, ethanol, isopropanol, butanediol and mixtures thereof. Solvents can be included in the overall composition in amounts ranging from 0.1% to 99% and preferably from 2.0% to 75%. It is noted that compositions of the present invention can be produced in the form of an emollient. A wide variety of suitable emollients are known and may be used herein. In this regard, reference is made to U.S. Pat. No. 5,296,500, the disclosure of which is hereby incorporated by reference.

Alternatively, the present composition can be formulated as a lotion containing from about 0.0002% to about 10% by weight of a peptide composition of the invention, e.g. a sextapeptide of the invention, a linked sextapeptide of the invention, or a peptide mimetic of the sextapeptides or linked sextapeptides of the invention. Alternatively, a lotion can be formulated containing about 1-10 mg/mL rice bran extract, prepared, for example, by any of the methods described herein. Lotions and creams can be formulated as emulsions as well as solutions. Further, the product can be formulated from a solution carrier system as a cream. A cream comprising a composition of the present invention would preferably comprise from about 0.1% to 15% and preferably from 1% to 5% active ingredients. Final products may contain up to 10% by weight but preferably 0.001 to 5% of an active ingredient, though of course more concentrated or more dilute solutions may also be used in greater or lesser amounts. For example, an eye cream may comprise about 0.0012% (w/w) and a facial cream may comprise about 0.0003% (w/w) of a sextapeptide compound, a linked sextapeptide compound or peptide mimetic thereof, in an excipient.

The peptide compositions of the invention (0.0004%-0.002%) and plant extracts of the invention (about 1-10 mg/ml), in a suitable cream, lotion or ointment base, may be applied topically to help restore elastic fibers in aged, sun damaged or wounded skin.

Peptide compositions of the invention (0.0004%-0.002%) and plant extracts of the invention (about 1-10 mg/ml), in a suitable cream, lotion or ointment base, may be applied topically to dilate existing cutaneous small blood vessels for the purpose of healing decubitus or diabetic ulcers that result from the contraction of small vessels supplying blood to the skin.

The peptides of the invention (10-20 µg/mL) or plant extracts of the invention (1-10 mg/ml) may be injected into coronary arteries during balloon angioplasty, injected intravenously, or injected directly into myocardial post-infarct scar tissue during open hear surgery as a means of stimulating new elastogenesis that would lend strength and resiliency to the post-infarct scar of the human heart.

Both crude and chemically purified plant extracts or preparations can be used in topical application for healing of decubitus or diabetic ulcers that result from the contraction of small vessels supplying blood to the skin. Because sequential oxalic acid or trypsin digestion of rice bran reduced the molecular weight of peptides in rice bran preparations, we hypothesize that even large and insoluble elastin-like proteins will be eventually partially digested by enzymes released from dead cells and bacteria (always contaminating those open skin ulcerations) and deliver the desirable peptide that would stimulate relaxation and opening of contracted capillaries and stimulate production of new extracellular matrix rich of new elastin.

Manganese salts ($MnCl_2$, $MnSO_4$ and MnaPCA) and trivalent iron (Ferric Ammonium Citrate, FAC) have each been shown to individually stimulate the production and assembly of new tropoelastin into new elastic fibers. The compositions of the present invention may be formulated to further include a manganese component and/or a trivalent iron component. Additionally, compounds comprising sodium are suitable additives for therapeutic compositions of the present invention. Sodium has been linked to the stimulation of elastogenesis. Copper, an activator of lysyl oxidase (an enzyme that crosslinks tropoelastin molecules into insoluble polymeric elastin) is another suitable additive used in the therapeutic compositions of the present invention.

Optionally, a manganese component may be added to a composition of the invention. The manganese may be any manganese compound, or a pharmaceutically acceptable salt thereof, but preferably is $MnCl_1$, $MnSO_4$ and/or MnPCA, wherein the manganese component is typically present in an amount from about 0.5 to 10 weight percent, preferably from about 1 to 8 weight percent and most preferably from about 5 to 7 weight percent, wherein the manganese is present in an amount from about 5 to 20 weight percent of a complex.

Optionally a trivalent iron component (such as, but not limited to, Ferric Ammonium Chloride (FAC) may also be included in the pharmaceutical composition. The trivalent iron component stimulates new elastogenesis and assists in treatment of elastic tissue defects. The trivalent iron, when included in the composition, is generally present in an amount from about 5 to 20 weight percent. In one embodiment the trivalent iron component is generally present in an amount from about 0.01 to 5 weight percent, preferably from about 0.02 to 3 weight percent, and more preferably from about 0.03 to 2 weight percent of the composition.

Optionally, a sodium component, or pharmaceutically acceptable salt thereof, may also be included in a pharmaceutical composition of the invention. The sodium component is generally present in about 5 to 20 percent of the complex. The sodium component may generally be present in an amount of about 1 to 10 percent weight percent, or from about 5 to 7 percent weight of the composition.

A copper component may also be included in the pharmaceutical composition, and may be any copper compound or pharmaceutically acceptable salt thereof. The copper component inhibits elastase and assists in the treatment of elastic tissue defects. The copper compound may be in the form of copper sebacate. When included in a composition the copper component is generally present in an amount of about 5 to 20 weight percent of the copper compound, such as copper sebacate. The copper component is generally present in an amount of about 0.01 to 5 percent weight or from about 0.03 to 2 percent weight of the composition.

It is contemplated that as one embodiment, the active ingredients described above be used as a lotion or cream emulsion of the oil-in-water type or as a water-in-oil type, both of which being extremely well known in the cosmetic field. Multiphase emulsions such as the water-in-oil type is disclosed in U.S. Pat. No. 4,254,105, the disclosure of which is incorporated herein by reference.

It is further contemplated that the active ingredients of the present invention be formulated from a solution carrier system as an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may comprise from 1% to 99% of an emollient plus to about 0.1% to 99% of a thickening agent. Reference is again made to U.S. Pat. No. 5,296,500 and the citations contained therein for a more complete disclosure of the various ointment, cream and lotion formulations for use herein.

The present composition can include one or more of a variety of optional ingredients, such as, but not limited to, anti-inflammatory agents, sunscreens/sunblocks, stimulators of protein synthesis, cell membrane stabilizing agents (i.e., carnitine), moisturizing agents, coloring agents, opacifying agents and the like, so long as they do not interfere with the elastin receptor binding properties of the sextapeptide compounds, or peptide mimetics thereof.

Additional components of the therapeutic compositions may include any suitable additive that has been used in cosmetics or other skin care compositions. These include, but are not limited to aloe vera, antioxidants, azulene, beeswax, benzoic acid, beta-carotene, butyl stearate, camphor, castor oil, chamomile, cinnamate, clay, cocoa butter, coconut oil, cucumber, dihydroxyacetone (DHA), elastin, estrogen, ginseng, glutamic acid, glycerin, glycolic acid, humectant, hydroquinone, lanolin, lemon, liposomes, mineral oil, monobenzone, nucleic acids, oatmeal, paba, panthenol, petroleum jelly, propelene glycol, royal jelly, seaweed, silica, sodium lauryl sulfate sulfur, witch hazel, zinc, zinc oxide, copper, hyaluronic acid and shea butter.

The compositions comprising the synthetic sextapeptide, synthetic linked sextapeptides, peptide mimetic thereof, or chemically digested plant extracts may further comprise retinoic acid, excipients, or other additives. For example, retinoic acid acts to stimulate collagen production and may be useful as an additive to compositions of the present invention.

Additives which aid in improving the elasticity of elastin comprising tissues such as tretinoin, vitamin E, sources of copper, and/or magnesium ions, retinol, copper peptides, and any one of the 20 standard amino acids may also be added to the compositions of the present invention. Additives which induce deposition of tropoelastin on microfibril scaffolds, and compounds which induce lysyl oxidase activity, such as transforming growth factor beta-1 and copper (supra), may also be added to such compositions. Compositions of the present invention may include a therapeutically and biologically compatible excipient.

The formulation can also include other active ingredients, such as antibiotics, analgesics, anti-allergenics and the like. The formulation is commonly applied to the skin as a lotion or cream to be rubbed on body tissue over the desired area. For optimum efficacy treatment in accordance with the presented method should be initiated as early as possible following exposure to sunlight, or other radiation source, or to skin injury (wound, etc). The formulation is generally applied to the skin once or twice daily. As noted elsewhere herein, the present composition may also be used to inhibit and/or minimize the effects of aging and/or photo damage on the skin, as well as to prevent and/or treat scars (such as cutaneous hypertrophic scars).

Administration

Upon formulation, solutions will be administered in a manner compatible with the dosage formulation and in such amount as is therapeutically effective. The formulations are easily administered in a variety of dosage forms such as direct topical application, application via a transdermal patch and the like.

For topical administration in an aqueous solution, for example, the compositions of the invention may be used directly on the skin without any toxic effects to the patient. Alternatively, the compositions of the invention may be dissolved or resuspended in a suitable buffer prior to mixing, if necessary.

In general, routine experimentation will determine specific ranges for optimal therapeutic effect for each composition and each administrative protocol, and administration to specific individuals will be adjusted to within effective and safe ranges depending on the condition and responsiveness of the individual to initial administrations.

Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention. Various modifications and combinations of the illustrative embodiments, as well as other embodiments of the invention, will be apparent to persons skilled in the art upon reference to the description.

The compositions of the present invention induce synthesis and deposition of elastin and induce cellular proliferation in normal human dermal fibroblasts. The following effects in culture compositions are better understood in reference to the examples below.

EXAMPLE 1

Reagents.

Soluble and insoluble rice bran were obtained from CGS Group, Inc. VGVAPG was obtained from Sigma (St. Louis, Mo.). EBPL-1 (VGVAPGAAAAAVGVAPG) (SEQ ID NO. 10), EBPL-2 (IGVAPG) (SEQ ID NO. 13) and EBPL-3 (IG-VAPGAAAAAIGVAPG) (SEQ ID NO. 14) were organically synthesized according to our design by EZBIOLAB, Inc. All peptides were synthesized at 95% purity.

Preparation of Chemically Digested Soluble Rice Bran.

One Gram of Soluble Rice Bran (Nutri Select Soluble-Nutri Rice CDG Group Inc.) was suspended in 40 ml of 1M NaOH diluted in 80% ethanol and incubated for one hour. The preparation was then centrifuged at 4000 rpm for 10 min, the pellet was re-suspended in 20 ml of distilled water, dialyzed (MWCO 2000) overnight against distilled water and than lyophilized. The product was then re-suspended in 5 ml of 0.25M oxalic acid and boiled for 1 hour. After centrifugation at 4000 rpm for 10 min the supernatant No 1 was collected and remaining pellet was re-suspended again in 5 ml of 0.25M oxalic acid and boiled. This procedure was repeated three times until the entire material was dissolved. All subsequent supernatants were combined with supernatants No 1 and dialyzed against 5 changes of distilled water and then lyophilized. The resulting 130 mg of white water soluble powder (the chemically digested rice bran —CDRB) contained 5 mg pure protein. Alternatively, the rice bran samples were also digested with amylase (to remove starch) and then treated with Cyanogen Bromide (CNBr) to solubilize non-crosslinked proteins.

Western Blots.

Both soluble and insoluble rice bran were filtered through a 3,000 Da filtration membrane and 20 µg samples of each were separated by SDS-PAGE electrophoresis and transferred to nitrocellulose. The nitrocellulose was subjected to western blotting with anti elastin, anti-VGVAPG (BA4) antibody, and antibody raised to AKAAAKAAAKA (SEQ ID NO. 15) (domain on tropoelastin that may be engaged in formation of crosslinking desmosines from four lysines). See Starcher, B, Conrad, N., Hinek, A. and Hill, C. H., *Connect. Tissue Res.* 40:273-282 (1999).

Cell Cultures.

Biological effects of soluble rice bran, insoluble rice bran, VGVAPG, EBPL-1, EBPL-2 and EBPL-3 were tested in cultures of skin fibroblasts derived from healthy Caucasian females of different ages. Biological effects of chemically digested rice bran (CDRB) was tested in cultures of skin fibroblasts derived from punch biopsies of healthy skin from 37-year old Caucasian female. All fibroblasts were originally isolated by allowing them to migrate out of skin explants and then passaged by trypsinization and maintained in alpha-minimum essential medium supplemented with 20 mM Hepes, 1% antibiotics and antimycotics, 1% L-Glutamate and 2% fetal bovine serum (FBS). In all experiments except those using CDBR, consecutive passages 3-7 were tested. Cells were incubated in the presence and absence of VGVAPG (SEQ ID NO. 1) (5 µg/mL), EBPL-2 (5 µg/mL) and EBPL-3 (10 µg/mL). In experiments using CDRB cell passage 3 was tested, cells were densely plated ($50 \times 10^6$ cells/dish) to rich immediate confluency and than cultured for 7 days in the presence and absence of 25 µg/ml CDBR (added at day 1 and 3).

Assessment of Deposition of Elastic Fibers.

7-day-old confluent cultures of fibroblasts, which produce abundant ECM, were used. All cultures were fixed in cold 100% methanol at −20° C. for 30 min, blocked with 1% normal goat serum (NGS) and then incubated for 1 hour with 2 µg/ml of polyclonal antibodies to tropoelastin. All cultures were then incubated for an additional hour with appropriate fluorescein-conjugated secondary antibodies (GAR-FITC). Nuclei were counterstained with propidium iodide. Morphometric analysis of cultures immunostained with antibodies recognizing extracellular matrix components was performed using a computerized video analysis system (Image-Pro Plus software 3.0, Media Cybernetics, Silver Spring, Md.) as described previously. Means and standard deviations were calculated and statistical analyses were carried out by ANOVA.

Results and Discussion.

Western blots with polyclonal antibody to tropoelastin and monoclonal antibody BA4, recognizing VGVAPG (SEQ ID NO. 1) sequence on elastin and another sterically similar GXXPG (SEQ ID NO. 2) hydrophobic domains, indicated that both soluble and insoluble rice brans contain tropoelastin-like epitopes and other GXXPG (SEQ ID NO. 2) sequences. Additional immunoblotting with antibody raised to AKAAAKAAAKA also indicated that this domain, unique to tropoelastin, is also present in the chemically digested rice bran preparations (FIG. 10). Based on these and other results, the rice bran preparations of the invention appear to include an elastin-like peptide.

Incubating the filtered (<3,000 Da) soluble and insoluble rice bran with dermal fibroblasts revealed that both these preparations can induce deposition of elastic fibers in vitro (FIG. 1). FIG. 1 presents primary cultures of human dermal fibroblasts, derived from a 44 year-old female, maintained for 7 days in the presence or absence of soluble or insoluble rice bran (<3,000 Da). Cells were fixed and immunostained with anti-tropoelastin antibodies and fluorescein-conjugated secondary antibodies (GAR-FITC).

Since we have previously shown that elastin receptor (elastin binding protein) ligands are present in ProK-60 (bovine ligamentum nuchae proteolytic digest) and can stimulate elastogenesis, we ran a BLAST search for short, nearly identical, sequences resembling VGVAPG (SEQ ID NO. 1) that might also serve as ligands for the elastin binding protein, a major component of the cell surface elastin receptor. This search revealed the EBPL sequences VGAMPG (SEQ ID NO. 4), VGLSPG (SEQ ID NO. 5), IGAMPG (SEQ ID NO. 6), IGLSPG (SEQ ID NO. 7), and IGVAPG (SEQ ID NO. 1) in protein derived from rice (*Oryza sativa*). Both IGVAPG (SEQ ID NO. 13) (EBPL-2) and its duplex polymer, IGVAP-GAAAAAIGVAPG (SEQ ID NO. 14) (EBPL-3), were organically synthesized and then tested in primary cultures of dermal fibroblasts. We hypothesized that both of these synthetic peptides would spontaneously fold into three-dimensional structures capable of interacting with the cell surface elastin receptor, and in turn, stimulate elastogenesis as VGVAPG (SEQ ID NO. 1) does. While not wishing to be bound by theory, it appears from our experiments that all synthetic EBPLs stimulated elastogenesis through interaction with the cell-surface elastin receptor (EBP=elastin binding protein) in a dose dependant manner.

Immunostaining with anti elastin antibody of 7 day-old primary cultures of dermal fibroblasts incubated in the presence of tested reagents demonstrated that our new synthetic peptides EBPL-2 and EBPL-3 are capable of inducing elastogenesis to the levels that exceed those obtained in cultures treated with VGVAPG (SEQ ID NO. 1) or with synthetic peptide containing its doublet VGVAPGAAAAAVGVAPG (SEQ ID NO. 10) (EBPL-1) (FIG. 2). FIG. 2 presents primary cultures of human dermal fibroblasts, derived from 38 and 44 year-old females, maintained for 7 days in the presence or absence of VGVAPG (SEQ ID NO. 1) (5 µg/mL), EBPL-2 (5 µg/mL) and EBPL-3 (10 µg/mL). Cells were fixed and immunostained with anti-tropoelastin antibodies and fluorescein-conjugated secondary antibodies (GAR-FITC). Interestingly, fibroblasts stimulated with VGVAPG (SEQ ID NO. 1) and EBPL-1 demonstrated very thin extracellular elastic fibers at levels greater than the control levels, whereas EBPL-2- and EBPL-3-treated cultures demonstrated deposition of thick extracellular elastic fibers. These results indicate that synthetic peptides reflecting the rice-derived sequence strongly stimulate elastogenesis and justify the above described effect obtained in cultures exposed to crude protein extracts from rice bran.

These preliminary data suggest that both EBPL-2 and EBPL-3 (containing IGVAPG (SEQ ID NO. 13) sequences mimicking the elastin receptor-binding domain, detected in the elastin-like rice bran derived protein) induce elastogenesis in dermal fibroblasts through their interaction with the cell-surface elastin receptor. We propose that, in contrast to full length tropoelastin or high molecular constructs reflecting tropoelastin exons, the small molecular weight synthetic peptides EBPL-2 and EBPL-3 (that can more easily penetrate through the epidermis) can constitute novel biologically active ingredients that can be formulated into suitable topical cosmetic anti-aging creams/lotions aimed at restoration of elastic fibers.

EXAMPLE 2

Production of new elastic fibers was also monitored by metabolic labeling tropoeelastin produced by cultured fibroblasts and its subsequent incorporation into insoluble elastin, the major component of elastic fibers. Fibroblasts were densely plated (50×105/dish) and grown to confluency in 10 cm cell culture dishes in quadruplicate. 20 µCi of [$^3$H]-valine was added to each dish along with fresh media. Cultures were then incubated for 72 hours and insoluble elastin was assessed separately in each culture. After media was removed, the cell layers and deposited extracellular matrix were scraped in 0.1N NaOH, sedimented by centrifugation, and boiled in 0.5 mL of 0.1N NaOH for 45 minutes to solubilize all matrix components except elastin. The resulting pellets containing the insoluble elastin were then solubilized by boiling in 200 µL of 5.7 N HCl for 1 hour and the aliquots were mixed with scintillation fluid and counted.

Figure 3:
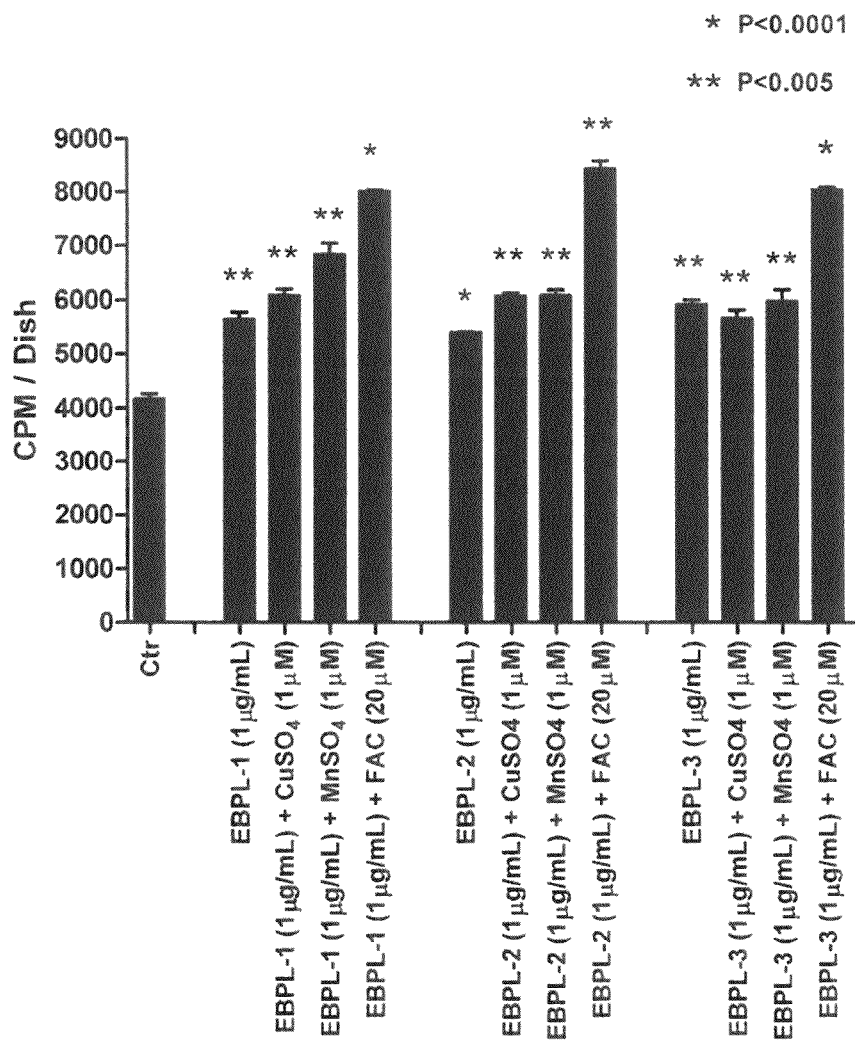
FIG. 3. Quantitative assessment of [$^3$H]-valine incorporation into newly deposited insoluble elastin in dermal fibroblast cultures maintained for 6 days with (SEQ ID NO. 2) GXXPG-containing peptides alone and in combination with copper, manganese and iron salts.

FIG. 3 shows the quantitative assessment of [$^3$H]-Valine incorporation into newly deposited insoluble elastin in dermal fibroblast cultures. Fibroblast cultures were stimulated daily for six days with GXXPG-containing peptides alone and in combination with copper, manganese and iron salts. These results show that the addition of metal salts enhances peptide-induced deposition of insoluble elastic fibers in vitro.

Figure 4:
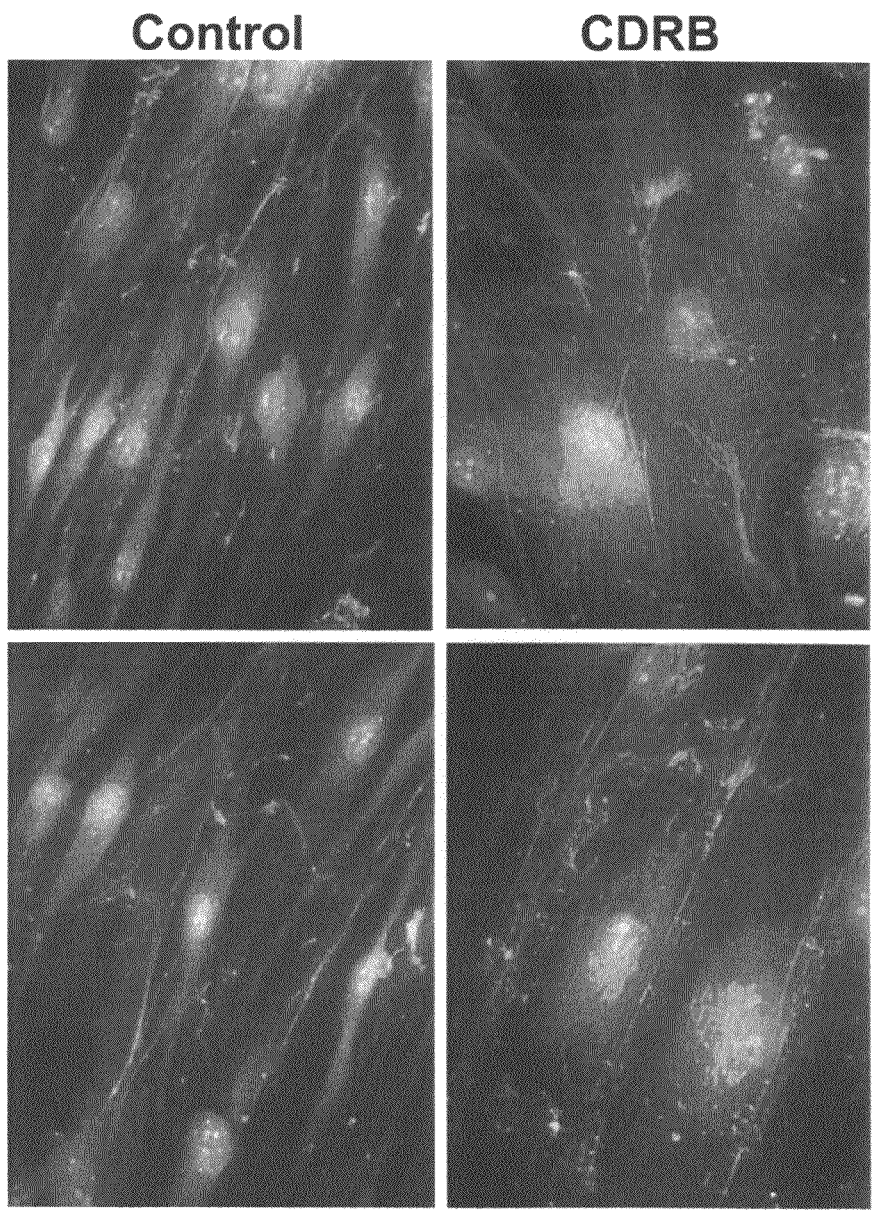
FIG. 4. Elastin deposition in 7 day old dermal fibroblast cultures in the presence and absence of chemically digested rice bran (CDRB). Two representative micrographs are shown for each condition.

FIG. 4 shows elastin deposition in 7 day-old dermal fibroblasts cultures in the presence and absence of CDRB. The CDRB treated cultures synthesize more tropoelastin (detected intracellularly) and deposit more extracellular elastic fibers as compared to control cultures.

EXAMPLE 3

Immunocytochemistry of 7 day-old fibroblast cultures with anti-tropoelastin antibody demonstrated that dermal fibroblasts derived from a female patient with stretch marks produced significantly more elastic fibers when treated with the chemically digested rice bran (CDRB). The CDRB-treated fibroblasts also demonstrated more immuno-detectable tropoelastin in their intracellular Golgi compartment than the untreated control fibroblast.

Preliminary immunocharacterization of CDRB showed immunoreactivity with a polyclonal elastin antibody, suggesting that CDRB may contain similar secondary structures found in mammalian elastin.

Data demonstrates that the rice-based peptides are much more (>500%) potent elastogenic inducers than ProK-60. This was confirmed through indirect immuno-fluorescence. Results were confirmed with Northern Blots and metabolic labeling of insoluble elastin (data not shown).

EXAMPLE 4

Figure 5:
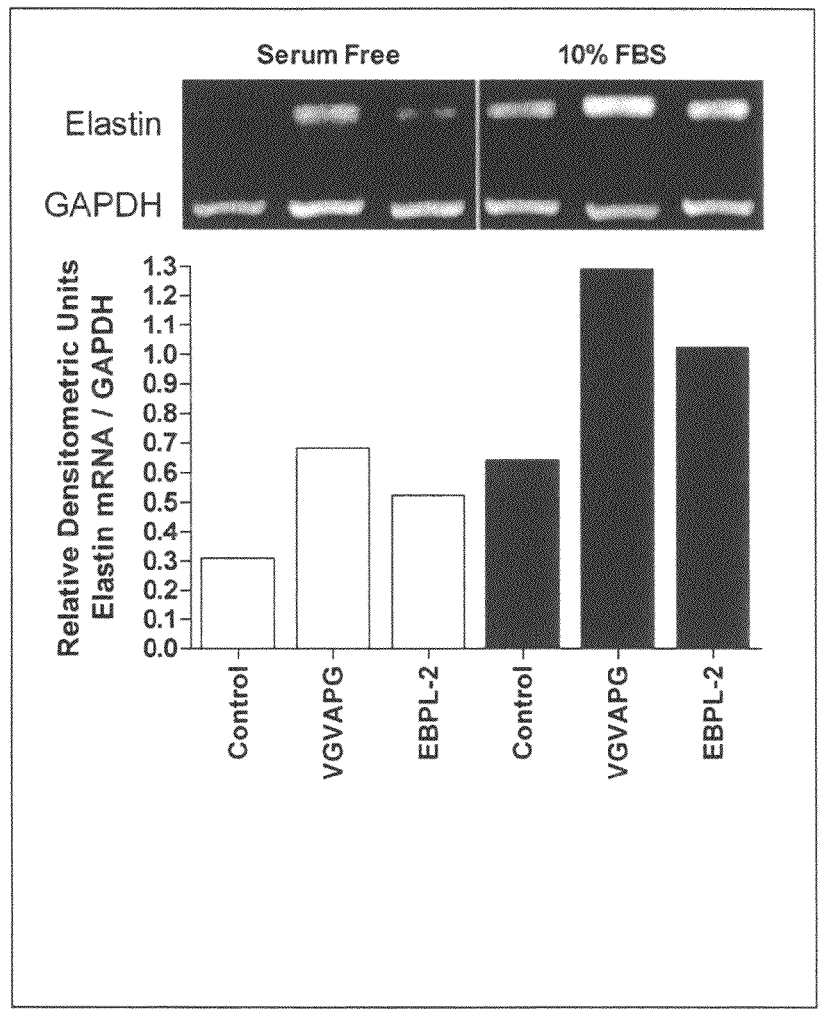
FIG. 5. Results of RT-PCR using specific tropoelastin probe indicate that EBPL-2 and VGVAPG (SEQ ID NO. 1) stimulated transcription of the elastin gene in adult dermal fibroblasts maintained in serum-free medium and media supplemented with 10% fetal bovine serum (FBS).

Using a BLAST search (ncbi.nlm.hih.gov/BLAST/) we identified the IGVAPG (SEQ ID NO. 13) domain in the amino acid sequence for a transcription factor of Japanese rice, which also reflects the common EBP-binding GXXPG (SEQ ID NO. 2) motif found in elastin and laminin. We used RT-PCR to measure transcription of the elastin gene by peptides of the invention. FIG. 5 shows that the synthetic hexapeptide, IGVAPG (SEQ ID NO. 13), (Code Name: EBPL-2™) increased transcription of the elastin gene as does VGVAPG (SEQ ID NO. 1) in cultures of adult dermal fibroblasts. The fact that both EBPL-2 and VGVAPG (SEQ ID NO. 1) stimulated transcription in adult dermal fibroblasts maintained in serum-free medium is indicative that both peptides are primary stimulators of elastogenesis. We also found that the observed higher levels of elastin mRNA were indeed translated into higher levels of tropoelastin protein (monomeric precursor of elastin).

EXAMPLE 5

Figure 6:
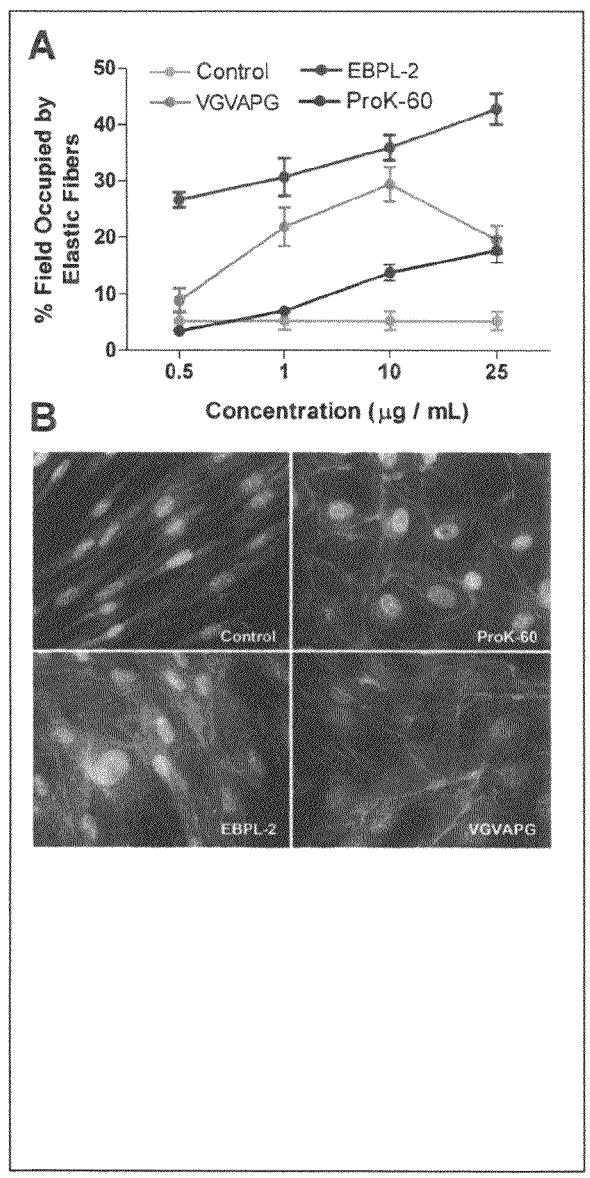
FIG. 6. (A) Results of Morphometric analysis of 7 day old cultures immunostained with anti-elastin antibody indicate that EBPL-2 and VGVAPG (SEQ ID NO. 1) treated adult dermal fibroblasts maximally produced 710% and 457% more elastic fibers, respectively, than control cultures as assessed by quantitative morphometric analysis of immuno-detectable tropoelastin. EBPL-2-treated fibroblasts maximally produced 141% more tropoelastin than maximum ProK-60-induced levels. (B) Representative micrographs depicting immuno-detectable elastic fibers (green) in cultures of normal dermal fibroblasts (derived from 55 old male), maintained for 7 days in the presence and absence of ProK-60-(25 µg/mL), EBPL-2-(25.1 g/mL) or VGVAPG (SEQ ID NO. 1) (10 µg/mL).

Culturing adult dermal fibroblasts in the presence of EBPL-2 and VGVAPG (SEQ ID NO. 1) for 7 days yielded enhanced levels of intra- and extracellular tropoelastin, as confirmed by immunocytochemical staining with an anti-tropoelastin antibody (FIG. 6). (A) As depicted in FIG. 6 (A) EBPL-2 and VGVAPG (SEQ ID NO. 1) treated adult dermal fibroblasts maximally produced 710% and 457% more tropoelastin, respectively, than control cultures as assessed by quantitative morphometric analysis of immuno-detectable tropoelastin. EBPL-2-treated fibroblasts maximally produced 141% more tropoelastin than maximum ProK-60-induced levels. (B) Representative tropoelastin immunostains of control, ProK-60-(25 µg/mL), EBPL-2-(25 µg/mL) and VGVAPG (SEQ ID NO. 1) (10 µg/mL)-treated adult dermal fibroblasts. Interestingly, fibroblasts stimulated with EBPL-2 demonstrated higher net deposition of tropoelastin than their counterparts cultured with VGVAPG (SEQ ID NO.1).

Figure 7:
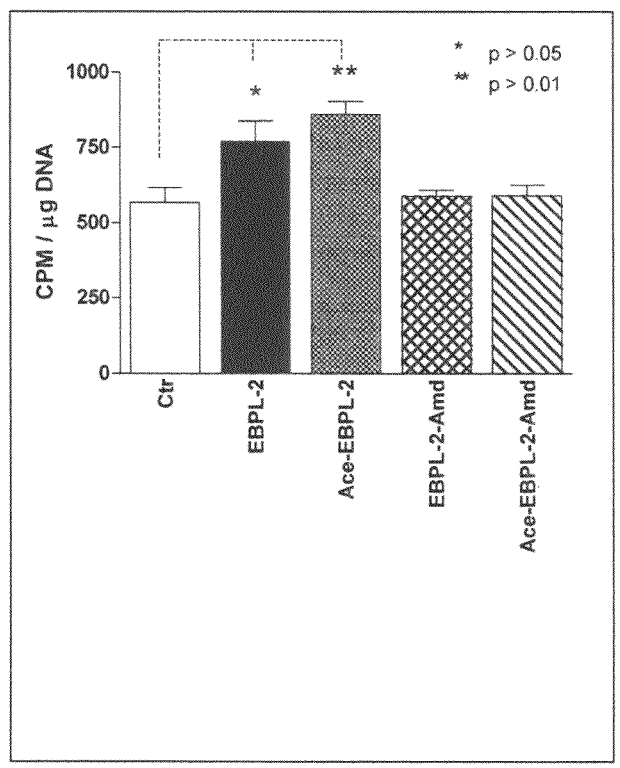
FIG. 7. Results of three independent experiments in which confluent cultures of human fibroblasts derived from normal human skin were metabolically labeled with [$^3$H]-Valine for 3 days and then assessed for the content of the newly deposited (radioactive) NaOH-insoluble elastin. Statistical analysis indicated that EBPL-2 (10 µg/mL)- and acetylated-EBPL-2 (Ace-EBPL-2, 10 µg/mL)-stimulated adult dermal fibroblasts deposited 36% and 51% more radioactively labeled insoluble elastin, respectively, as compared to non-treated fibroblasts. Amidated EBPL-2 did not enhance deposition of insoluble elastin.
Figure 8:
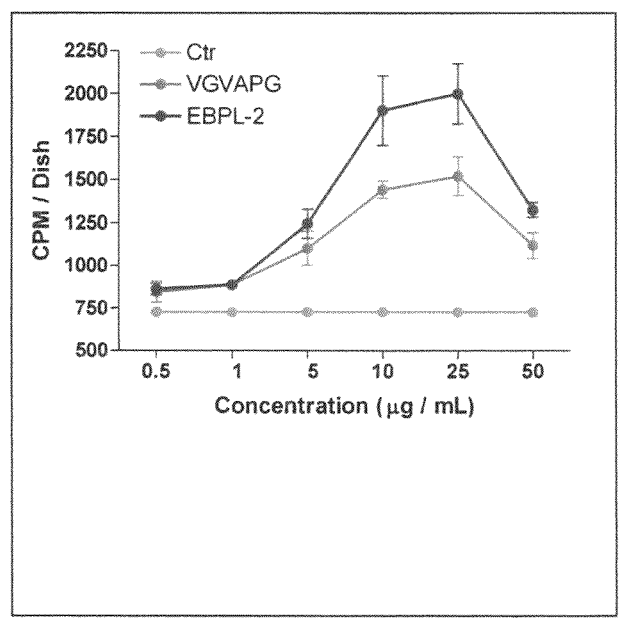
FIG. 8. Results of three independent experiments in which confluent cultures of human fibroblasts derived from normal human skin were metabolically labeled with [$^3$H]-Valine for 3 days and then assessed for the content of the newly deposited (radioactive) NaOH-insoluble elastin. Statistical analysis indicates that both VGVAPG (SEQ ID NO. 1) and EBPL-2 enhanced net deposition of insoluble elastin in a dose dependent manner and that the effect of the EBPL-2 (maximum 175% over control values) significantly exceeded the effect induced by VGVAPG (SEQ ID NO. 1) (maximum 109% over control values).

Since EBPL-2 efficiently stimulated tropoelastin production, we next tested whether this monomer precursor can be efficiently incorporated into the cross-linked insoluble elastin, a major component of elastic fibers. Results of metabolic labeling of cultured dermal fibroblasts with [$^3$H]-valine, followed by assay of NaOH-insoluble elastin (normalized per DNA content) indicated that fibroblasts maintained for 7 days in the presence of EBPL-2 or its acetylated version produce more elastin (FIG. 7). Acetylating the N-terminus of EBPL-2 appeared to enhance its biological activity, although not statistically different than non-acetylated EBPL-2. On the other hand, amidating the C-terminus of EBPL-2 abolished its biological activity, indicating that the C-terminal glycine is imperative to the overall secondary structure of EBPL-2 that permits binding to the EBP and induction of elastogenesis. Additional quantification of the newly deposited insoluble elastin (expression of the obtained results per culture dish) demonstrated an even more spectacular net increase in metabolically labeled insoluble elastin (FIG. 8).

Results of this calculation, showing a more profound effect of EBPL-2 on net deposition of insoluble elastin per culture, led to the hypothesis that EBPL-2, similarly to VGVAPG (SEQ ID NO. 1), also stimulates cellular proliferation. This assumption was later confirmed by a direct quantification of cellular proliferation showing higher than control incorporation of [$^3$H]-thymidine by dermal fibroblasts treated with EBPL-2 and VGVAPG (SEQ ID NO. 1).

EXAMPLE 6

Figure 9:
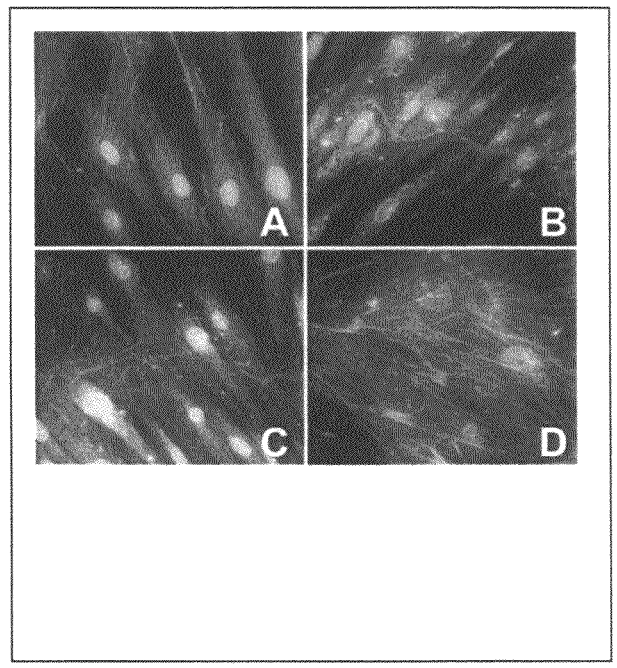
FIG. 9. Representative micrographs depicting immunostained (green) elastic fibers deposited in 7 day old cultures of normal skin human fibroblasts. The rice bran extract sequentially digested with oxalic acid (D) induced more production of tropoelastin than whole insoluble (B) and soluble (C) rice bran in 7 day-old cultures of adult dermal fibroblasts as compared to control cultures (A).

In a separate series of experiments we also tested whether protein extracts of rice bran would reveal active GXXPG-like sequences capable of inducing elastogenesis in dermal fibroblast cultures. First, we demonstrated by Western blotting that insoluble and soluble fractions of rice bran contained GXXPG (SEQ ID NO. 2) epitopes that were immuno-reactive with anti-tropoelastin and anti-VGVAPG antibodies. Furthermore we found that a chemical digest of rice bran, which was enriched in elastin-like NaOH-insoluble protein, demonstrated similar results. Final experiments revealed that all rice bran-derived preparations enhanced deposition of tropoelastin by cultured adult dermal fibroblasts (FIG. 9).

EXAMPLE 7

The following procedures, although not intended to limit the scope of the invention, were used to prepare chemically digested rice bran extracts:
Protocol A 50 grams of soluble Rice Bran- (Nutri Rice CDC Group Inc)
Dissolve in 160 ml 80% Ethanol + 40 ml Acetone
Incubation 30 Min in 37° C., Discard supernatant, and save the pellet
Dissolve the pellet in 100 ml of 1M NaOH diluted in distilled water,
Boil for 60 min.
Centrifuge at 4000 rpm for 10 min, discard supernatant
Wash the pellet with distilled water 4 times
Dissolve the pellet in 100 ml of 0.25M Oxalic acid
Boil for 60 min
Centrifuge at 4000 rpm for 10 min    Collect supernatant 1
Dissolve the pellet in 100 ml of 0.25M Oxalic acid
Boil for 60 min
Centrifuge at 4000 rpm for 10 min    Collect supernatant 2

-continued

Dissolve the remaining pellet in 50 ml of 0.25M Oxalic acid
Boil for 60 min
Centrifuge at 4000 rpm for 10 min    Collect supernatant 3
Combine collected supernatants 1, 2, 3
Dialyze against 5 changes of distilled water
Lyophilize
Final powder: 230 mg, concentration of pure protein: 0.342 ug/mg Protocol B 50 grams of Insoluble Rice Bran -(Nutri Rice CDC Group Inc.)
Dissolve in 160 ml 80% Ethanol + 40 ml Acetone
Incubate 30 Min in 37° C., Discard supernatant, and save the pellet
Dissolve the pellet in 400 ml of 1M NaOH diluted in distilled water,
Boil for 60 min.
Add 100 ml of 1M NaOH diluted in distilled water
Boil for 60 min
Centrifuge at 4000 rpm for 10 min, discard supernatant
Wash the pellet with distilled water 4 times
Dissolve the pellet in 300 ml of 0.25M Oxalic acid
Boil for 60 min
Centrifuge at 4000 rpm for 10 min    Collect supernatant 1
Dissolve the pellet in 200 ml of 0.25M Oxalic acid
Boil for 60 min
Centrifuge at 4000 rpm for 10 min    Collect supernatant 2
Dissolve the remaining pellet in 150 ml of 0.25M Oxalic acid
Boil for 60 min
Centrifuge at 4000 rpm for 10 min    Collect supernatant 3
Combine collected supernatants 1, 2, 3
Dialyze against 5 changes of distilled water
Lyophilize (96 hr)
Final powder: 201 mg, concentration of pure protein 8.89 ug/mg Protocol C
100 mg Extracted soluble Rice Bran pellet
Dissolve in 5 ml Amylase (1000 U/ml)
Incubate 72 hr at 37° C. and shake
Centrifuge at 1500 rpm for 10 min
Collect supernatant
Dialyze against 3 changes of distilled water
Lyophilize
Dissolve final powder in 200 ul distilled water, concentration of pure protein 1.42 ug/ul
Protocol D
100 mg Extracted Insoluble Rice Bran pellet
Dissolve in 10 ml Amylase (1000 U/ml)
Incubate 72 hr at 37° C. and shake
Centrifuge at 1500 rpm for 10 min
Collect supernatant
Dialyze against 3 changes of distilled water
Lyophilize
Dissolve final powder in 200 ul distilled water, concentration of pure protein 0.16 ug/ul
Protocol E 10 grams of Soluble Rice Bran, - (Nutri Rice CDC Group Inc)
10 grams of Insoluble Rice Bran, - (Nutri Rice CDC Group Inc
Dissolve in 40 ml Amylase (1000 U/ml)
Incubate 5 days at 37° C. and shake
Dialyze against 3 changes of distilled water
Add 40 ml 80% Ethanol + 10 ml Acetone
Incubate 30 Min at 37° C.,
Centrifuge at 4000 rpm for 10 min and save the pellet
Dissolve the pellet in 40 ml of 1M NaOH diluted in distilled water,
Boil for 60 min.
Centrifuge at 4000 rpm for 10 min, discard supernatant
Wash the pellet with distilled water 4 times
Dissolve the pellet in 40 ml of 0.25M Oxalic acid -continued Boil for 60 min
Centrifuge at 4000 rpm for 10 min          Collect supernatant 1
Dissolve the pellet in 40 ml of 0.25M Oxalic acid
Boil for 60 min
Centrifuge at 4000 rpm for 10 min          Collect supernatant 2
Dissolve the remaining pellet in 20 ml of 0.25M Oxalic acid
Boil for 60 min
Centrifuge at 4000 rpm for 10 min          Collect supernatant 3
Combine collected supernatants 1, 2, 3
Dialyze against 5 changes of distilled water
Lyophilize (96 hr)
Take 5 mg of Final powder and dissolve in 100 ul distilled water
Concentration of protein:     Soluble rice: 3.44 ug/ul
                               Insoluble rice: 0.217 ug/ul Protocol F 3 grams of Soluble Rice Bran, -(Nutri Rice CDC Group Inc)
3 grams of Insoluble Rice Bran, -(Nutri Rice CDC Group Inc)
Make 70% formic acid and bubble nitrogen through it to remove the oxygen (CNBr does not work in the presence of oxygen)
In the fume hood, using a disposable tube, weight 2 gm of Cyanogen Bromide (CNBr) to make a 40 ml solution when dissolve in the formic acid (50 mg/ml)
Add 20 ml of solution to 3 gm soluble rice bran and 3 gm insoluble rice bran respectively
Close lid and leave in the fume hood to digest overnight
Next day, use boiling water to wash digests 5 times in the fume hood
Centrifuge at 3300 rpm for 10 min in the fume
Save pellet
Half of pellet should be lyophilized
Half of pellet should be dissolve in 20 ml M NaOH and boiled for 60 min
For Soluble rice pellet: Add 30 mL distilled water and dialyze against 3 changes of distilled water
lyophilize
For Insoluble Rice pellet:
Wash with distilled water 3 times
Dialyze against 3 changes of distilled water
Lyophilize
Take 2 mg of each final powder, dissolve in 100 ul distilled water, Concentration of protein:
1, CNBr digested soluble rice: 3.7 ug/ul
2, CNBr digested insoluble rice: out of range
3, CNBr+NaOH Soluble rice: out of range
4, CNBr+NaOH Insoluble rice: 7.03 ug/ul
Protocol G Starting material: 1 gram of Soluble Rice Bran (Nutri Select Soluble-Nutri Rice CDG Group Inc.)
Dissolve in 40 ml of 1 M NaOH diluted in 80% Ethanol
Centrifuge at 4000 rpm for 10 min. and save the pellet
Dissolve pellet in 20 ml of distilled water -continued Dialyze overnight against distilled water (MWCO 2000)
Lyophilize (48 hours)
Dissolve the lyophilized powder in 5 ml of 0.25M Oxalic acid
Boil for 1 hour
Centrifuge at 4000 rpm for 10 min.
                               Collect supernatant 1
Dissolve the pellet in 5 ml of 0.25M Oxalic acid
Boil for 1 hour
Centrifuge at 4000 rpm for 10 min
                               Collect supernatant 2
Dissolve the remaining pellet in 5 ml of 0.25M Oxalic acid
Boiling for 1 hour
Centrifuge at 4000 rpm for 10 min
                               Collect supernatant 3
Combine collected supernatants 1, 2, 3
Dialyze against 5 changes of water
Lyophylize (48 hours)

Both Amylase-digested soluble and insoluble rice bran preparations contain proteins that react with antibody raised to human tropoelastin (FIG. 10). Additionally, the soluble bran preparation also contains a peptide with the unique AKAAAKAAAKA (SEQ ID NO. 15) domain detected in tropoelastin.

Figure 11:
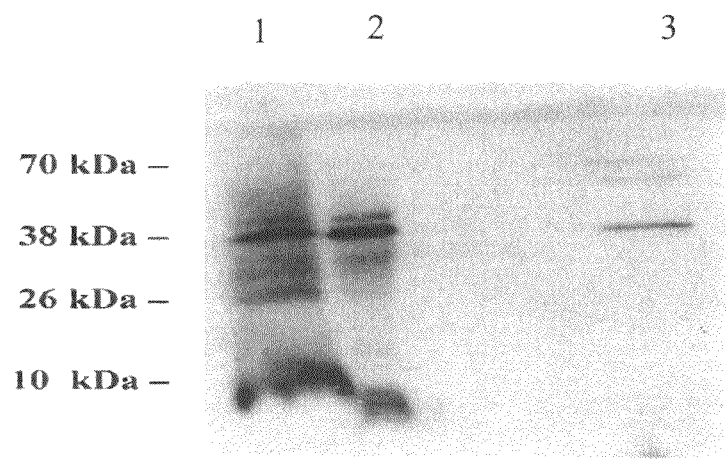
FIG. 11. Western blotting with anti-tropoelastin antibody demonstrating that CNBr digests of rice bran preparations contain protein(s) with similar immunoreactivity as human 70-kDa tropoelastin and its degradation products. 1: Cyanogen bromide digest of soluble rice bran. 2: Cyanogen bromide digest of insoluble rice bran. 3: Extract from culture of elastin-producing human fibroblasts.

Western blotting with anti-tropoelastin antibody demonstrated that samples of CNBr digests of rice bran preparations contain protein(s) with similar immunoreactivity as human 70-kDa tropoelastin and its degradation products (FIG. 11). 1: Cyanogen bromide digest of soluble rice bran. 2: Cyanogen bromide digest of insoluble rice bran. 3: Extract from culture of elastin-producing human fibroblasts.

EXAMPLE 8

Figure 12:
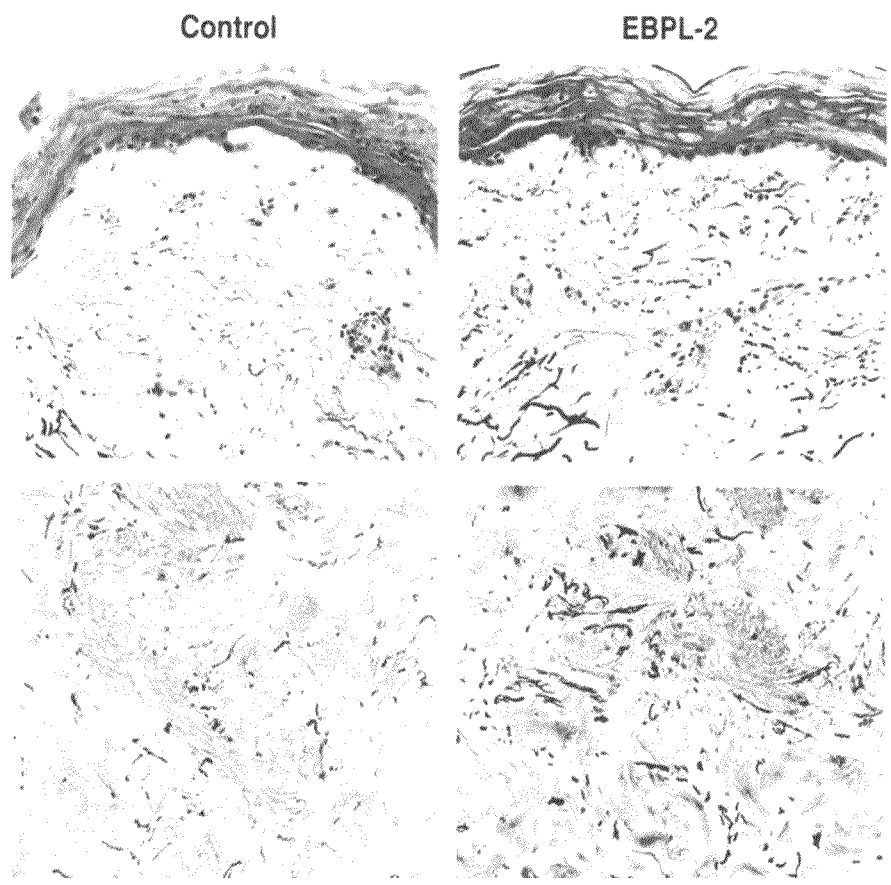
FIG. 12. Representative micrographs of 10-day old organ cultures of human skin explants (44 year woman) stained with Movat pentachrome stain. Cultures treated with EBPL-2 contained more elastic fibers (black stain) produced by cells migrating out of the basal layer of the epidermis, which contain multi-potential stem cells (Upper panel) and by myofibroblasts localized in the deeper dermal zone (Lower panel).

FIG. 12 shows representative micrographs of 10-day old organ cultures of human skin explants (44 year woman) stained with Movat pentachrome stain. Cultures treated with EBPL-2 contained more elastic fibers (black stain) produced by cells migrating out of the basal layer of the epidermis (upper panel) and by myofibroblasts localized in the deeper dermal zone (lower panel).

EXAMPLE 9

Figure 13:
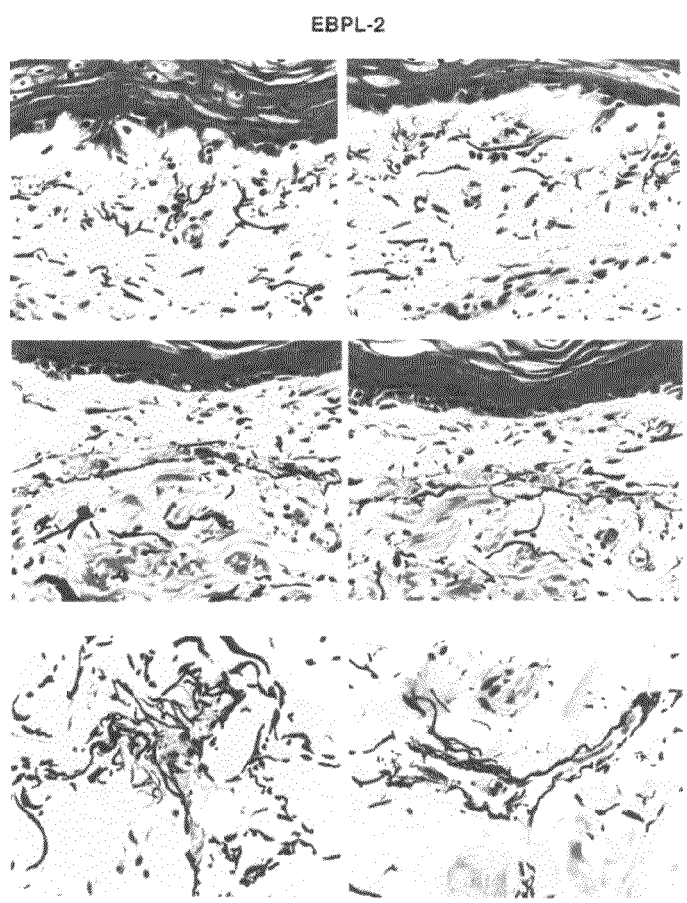
FIG. 13. Multiple micrographs demonstrating that treatment with EBPL-2 induced dilatation of the existing dermal capillaries, and stimulated production of new elastic fibers by pericytes, cells located in the peripheral layer of those capillaries.

EBPL-2 stimulates dilatation of existing capillaries in organ cultures of human skin biopsies. FIG. 13 shows multiple micrographs demonstrating that treatment with EBPL-2 induce dilatation of capillaries which pericytes produce elastic fibers.

Figure 14:
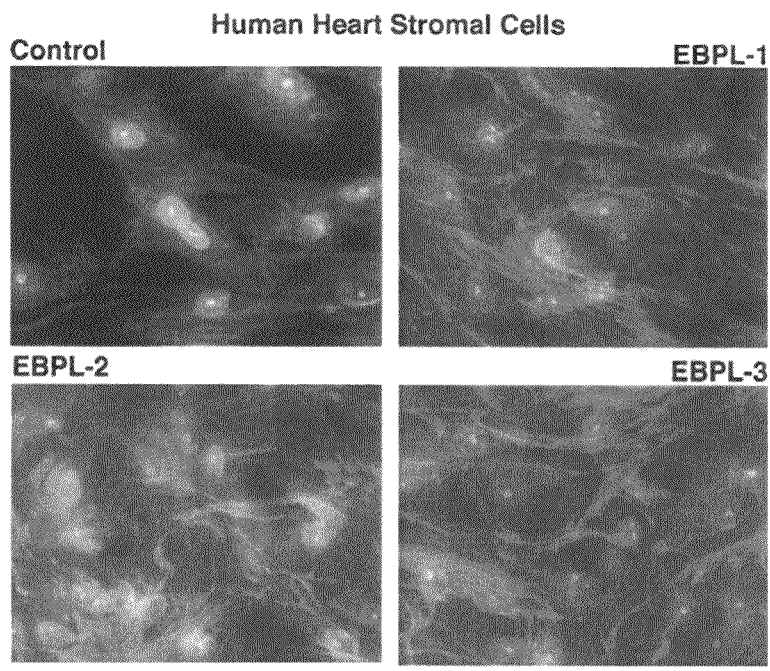
FIG. 14. Representative micrographs of 7 day old cultures of human heart stromal cells. The micrographs of FIG. 14 demonstrate that synthetic EBPL peptides significantly increased production of elastic fibers by stromal cells isolated from human heart.

EBPL-peptides stimulate elastogenesis in human heart stromal cells. The micrographs of FIG. 14 demonstrate that synthetic EBPL peptides significantly increase production of elastic fibers by stromal cells isolated from human heart.

Although the present invention has been described in considerable detail with reference to certain preferred embodiments thereof, other versions are possible. Therefore the spirit and scope of the appended claims should not be limited to the description and the preferred versions contain within this specification.

What is claimed is:

1. A method of stimulating elastogenesis comprising administering a therapeutically effective amount of a composition comprising a synthetic sextapeptide having a sequence $X_1$-$X_2$-$X_3$-$X_4$-$X_5$-$X_6$ (SEQ ID NO. 3), wherein:
   $X_1$ is V or I;
   $X_2$ is G;
   $X_3$ is A or L;
   $X_4$ is M or S;
   $X_5$ is P; and
   $X_6$ is G; and
   wherein the administering includes at least one of topical application and application via a transdermal patch.

2. The method of claim 1, wherein the synthetic sextapeptide is selected from the group consisting of VGAMPG (SEQ ID NO. 4), VGLSPG (SEQ ID NO. 5), IGAMPG (SEQ ID NO. 6), and IGLSPG (SEQ ID NO. 7).

3. The method of claim 1 wherein the composition provides an appearance of increased elastogenesis in a tissue.

4. The method of claim 1 wherein the composition stimulates proliferation and migration of dermal fibroblasts into an area of skin.

5. The method of claim 1 wherein the composition provides an enhanced deposition of elastin in a tissue.

6. The method of claim 1 wherein the composition improves the appearance of skin.

7. A method of stimulating elastogenesis comprising administering a therapeutically effective amount of a composition comprising a synthetic linked sextapeptide having a sequence $X_1$-$X_2$-$X_3$-$X_4$-$X_5$-$X_6$,-$X_7$-$X_1$-$X_2$-$X_3$-$X_4$-$X_5$-$X_6$ (SEQ ID NO. 16) wherein:
   $X_7$ is a linking moiety;
   $X_1$ is independently selected from V and I;
   $X_2$ is G;

$X_3$ is independently selected from A and L;
$X_4$ is independently selected from M and S;
$X_5$ is P; and
$X_6$ is G.

8. The method of claim 7 wherein the synthetic linked sextapeptide is selected from the group consisting of VGAMPGAAAAAVGAMPG (SEQ ID NO. 8), VGLSP-GAAAAAVGLSPG (SEQ ID NO. 9), IGAMP-GAAAAAIGAMPG (SEQ ID NO. 11), and IGLSP-GAAAAAIGLSPG (SEQ ID NO. 12).

9. The method of claim 7 wherein the composition provides an appearance of increased elastogenesis in a tissue.

10. The method of claim 7 wherein the composition stimulates proliferation and migration of dermal fibroblasts into an area of skin.

11. The method of claim 7 wherein the composition provides an enhanced deposition of elastin in a tissue.

12. The method of claim 7 wherein the composition improves the appearance of skin.

13. The method of claim 7 wherein the administering includes at least one of topical application and application via a transdermal patch.

14. The method of claim 7 wherein the linking moiety is selected from the group consisting of an amino acid, alanine, a disulfide bond, a carbonyl moiety, a hydrocarbon moiety optionally substituted at one or more available carbon atoms with a lower alkyl substituent, a lysine residue and a lysine amide.

* * * * *

SEQUENCE LISTING

<160> NUMBER OF SEQ ID NOS: 18

<210> SEQ ID NO 1
<211> LENGTH: 6

```
<212> TYPE: PRT
<213> ORGANISM: Artificial Sequence
<220> FEATURE:
<223> OTHER INFORMATION: Synthetic derived from Oryza sativa

<400> SEQUENCE: 1

Val Gly Val Ala Pro Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic, wherein X is any amino acid
<220> FEATURE:
<221> NAME/KEY: misc_feature
<222> LOCATION: (2)..(3)
<223> OTHER INFORMATION: Xaa can be any naturally occurring amino acid

<400> SEQUENCE: 2

Gly Xaa Xaa Pro Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be V or I
<220> FEATURE:
<221> NAME/KEY: misc_feature
<222> LOCATION: (2)..(2)
<223> OTHER INFORMATION: Xaa is G
<220> FEATURE:
<221> NAME/KEY: misc_feature
<222> LOCATION: (3)..(3)
<223> OTHER INFORMATION: Xaa can be A or L
<220> FEATURE:
<221> NAME/KEY: misc_feature
<222> LOCATION: (4)..(4)
<223> OTHER INFORMATION: Xaa can be M or S
<220> FEATURE:
<221> NAME/KEY: misc_feature
<222> LOCATION: (5)..(5)
<223> OTHER INFORMATION: Xaa is P
<220> FEATURE:
<221> NAME/KEY: misc_feature
<222> LOCATION: (6)..(6)
<223> OTHER INFORMATION: Xaa is G

<400> SEQUENCE: 3

Xaa Xaa Xaa Xaa Xaa Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic derived from Oryza sativa

<400> SEQUENCE: 4

Val Gly Ala Met Pro Gly
1               5

<210> SEQ ID NO 5
<211> LENGTH: 6
```

```
<212> TYPE: PRT
<213> ORGANISM: Artificial Sequence
<220> FEATURE:
<223> OTHER INFORMATION: Synthetic derived from Oryza sativa

<400> SEQUENCE: 5

Val Gly Leu Ser Pro Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic derived from Oryza sativa

<400> SEQUENCE: 6

Ile Gly Ala Met Pro Gly
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic derived from Oryza sativa

<400> SEQUENCE: 7

Ile Gly Leu Ser Pro Gly
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic derived from Oryza sativa

<400> SEQUENCE: 8

Val Gly Ala Met Pro Gly Ala Ala Ala Ala Val Gly Ala Met Pro
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: Synthetic derived from Oryza sativa

<400> SEQUENCE: 9

Val Gly Leu Ser Pro Gly Ala Ala Ala Ala Val Gly Leu Ser Pro
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: Synthetic derived from Oryza sativa

<400> SEQUENCE: 10

Val Gly Val Ala Pro Gly Ala Ala Ala Ala Val Gly Val Ala Pro
1               5                   10                  15

Gly
```

```
<210> SEQ ID NO 11
<211> LENGTH: 17
<212> TYPE: PRT
<213> ORGANISM: Artificial Sequence
<220> FEATURE:
<223> OTHER INFORMATION: Synthetic derived from Oryza sativa

<400> SEQUENCE: 11

Ile Gly Ala Met Pro Gly Ala Ala Ala Ala Ile Gly Ala Met Pro
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Synthetic derived from Oryza sativa

<400> SEQUENCE: 12

Ile Gly Leu Ser Pro Gly Ala Ala Ala Ala Ile Gly Leu Ser Pro
1               5                   10                  15

Gly

<210> SEQ ID NO 13
<211> LENGTH: 6
<212> TYPE: PRT
<213> ORGANISM: Artificial Sequence
<220> FEATURE:
<223> OTHER INFORMATION: Synthetic derived from Oryza sativa

<400> SEQUENCE: 13

Ile Gly Val Ala Pro Gly
1               5

<210> SEQ ID NO 14
<211> LENGTH: 17
<212> TYPE: PRT
<213> ORGANISM: Artificial Sequence
<220> FEATURE:
<223> OTHER INFORMATION: Synthetic derived from Oryza sativa

<400> SEQUENCE: 14

Ile Gly Val Ala Pro Gly Ala Ala Ala Ala Ile Gly Val Ala Pro
1               5                   10                  15

Gly

<210> SEQ ID NO 15
<211> LENGTH: 11
<212> TYPE: PRT
<213> ORGANISM: Artificial Sequence
<220> FEATURE:
<223> OTHER INFORMATION: Synthetic derived from human tropelastin

<400> SEQUENCE: 15

Ala Lys Ala Ala Ala Lys Ala Ala Ala Lys Ala
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<222> LOCATION: (1)..(1)
<223> OTHER INFORMATION: Xaa is independently selected from V and I
<220> FEATURE:
<221> NAME/KEY: misc_feature
<222> LOCATION: (2)..(2)
<223> OTHER INFORMATION: Xaa is G
<220> FEATURE:
<221> NAME/KEY: misc_feature
<222> LOCATION: (3)..(3)
<223> OTHER INFORMATION: Xaa is independently selected from A and L
<220> FEATURE:
<221> NAME/KEY: misc_feature
<222> LOCATION: (4)..(4)
<223> OTHER INFORMATION: Xaa is independently selected from M and S
<220> FEATURE:
<221> NAME/KEY: misc_feature
<222> LOCATION: (5)..(5)
<223> OTHER INFORMATION: Xaa is P
<220> FEATURE:
<221> NAME/KEY: misc_feature
<222> LOCATION: (6)..(6)
<223> OTHER INFORMATION: Xaa is G
<220> FEATURE:
<221> NAME/KEY: misc_feature
<222> LOCATION: (7)..(7)
<223> OTHER INFORMATION: Xaa is a linking moiety
<220> FEATURE:
<221> NAME/KEY: misc_feature
<222> LOCATION: (8)..(8)
<223> OTHER INFORMATION: Xaa is independently selected from V and I
<220> FEATURE:
<221> NAME/KEY: misc_feature
<222> LOCATION: (9)..(9)
<223> OTHER INFORMATION: Xaa is G
<220> FEATURE:
<221> NAME/KEY: misc_feature
<222> LOCATION: (10)..(10)
<223> OTHER INFORMATION: Xaa is independently selected from A and L
<220> FEATURE:
<221> NAME/KEY: misc_feature
<222> LOCATION: (11)..(11)
<223> OTHER INFORMATION: Xaa is independently selected from M and S
<220> FEATURE:
<221> NAME/KEY: misc_feature
<222> LOCATION: (12)..(12)
<223> OTHER INFORMATION: Xaa is P
<220> FEATURE:
<221> NAME/KEY: misc_feature
<222> LOCATION: (13)..(13)
<223> OTHER INFORMATION: Xaa is G

<400> SEQUENCE: 16

Xaa Xaa Xaa Xaa Xaa Xaa Xaa Xaa Xaa Xaa Xaa Xaa Xaa
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is V or I or a mimetic of V or I
<220> FEATURE:
<221> NAME/KEY: misc_feature
<222> LOCATION: (2)..(2)
<223> OTHER INFORMATION: Xaa is G or a mimetic of G
<220> FEATURE:
<221> NAME/KEY: misc_feature
<222> LOCATION: (3)..(3)
<223> OTHER INFORMATION: Xaa is A or L or a mimetic of A or L
<220> FEATURE:
<221> NAME/KEY: misc_feature
<222> LOCATION: (4)..(4)
<223> OTHER INFORMATION: Xaa is M or S or a mimetic of M or S
```

```
<220> FEATURE:
<221> NAME/KEY: misc_feature
<222> LOCATION: (5)..(5)
<223> OTHER INFORMATION: Xaa is P or a mimetic of P
<220> FEATURE:
<221> NAME/KEY: misc_feature
<222> LOCATION: (6)..(6)
<223> OTHER INFORMATION: Xaa is G or a mimetic of G

<400> SEQUENCE: 17

Xaa Xaa Xaa Xaa Xaa Xaa
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is V or I or a mimetic of V or I
<220> FEATURE:
<221> NAME/KEY: misc_feature
<222> LOCATION: (2)..(2)
<223> OTHER INFORMATION: Xaa is G or a mimetic of G
<220> FEATURE:
<221> NAME/KEY: misc_feature
<222> LOCATION: (3)..(3)
<223> OTHER INFORMATION: Xaa is A or L or a mimetic of A or L
<220> FEATURE:
<221> NAME/KEY: misc_feature
<222> LOCATION: (4)..(4)
<223> OTHER INFORMATION: Xaa is M or S or a mimetic of M or S
<220> FEATURE:
<221> NAME/KEY: misc_feature
<222> LOCATION: (5)..(5)
<223> OTHER INFORMATION: Xaa is P or a mimetic of P
<220> FEATURE:
<221> NAME/KEY: misc_feature
<222> LOCATION: (6)..(6)
<223> OTHER INFORMATION: Xaa is G or a mimetic of G
<220> FEATURE:
<221> NAME/KEY: misc_feature
<222> LOCATION: (7)..(7)
<223> OTHER INFORMATION: Xaa is an alanine; where alanine serves as a
     site for joining one or more linking amino acid residues
     comprising alanine wherein the linking residues join two
     sextapeptide compounds to each other.

<400> SEQUENCE: 18

Xaa Xaa Xaa Xaa Xaa Xaa Xaa
1               5
```